US006831166B2

(12) United States Patent
Manoharan et al.

(10) Patent No.: US 6,831,166 B2
(45) Date of Patent: Dec. 14, 2004

(54) DERIVATIZED OLIGONUCLEOTIDES HAVING IMPROVED UPTAKE AND OTHER PROPERTIES

(75) Inventors: Muthiah Manoharan, Carlsbad, CA (US); Phillip Dan Cook, Carlsbad, CA (US); Clarence Frank Bennett, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 126 days.

(21) Appl. No.: 10/073,718

(22) Filed: Feb. 11, 2002

(65) Prior Publication Data

US 2002/0177150 A1 Nov. 28, 2002

Related U.S. Application Data

(60) Division of application No. 09/633,659, filed on Aug. 7, 2000, now Pat. No. 6,395,492, which is a division of application No. 08/211,882, filed on Apr. 22, 1994, now Pat. No. 6,153,737, which is a continuation-in-part of application No. PCT/US92/09196, filed on Oct. 23, 1992.

(51) Int. Cl.[7] ........................ C07H 19/00; C07H 21/00; C12Q 1/68; A01N 43/04
(52) U.S. Cl. ........................... 536/23.1; 514/1; 514/44; 435/6; 536/24.3; 536/25.3; 536/26.6
(58) Field of Search ..................... 435/5, 6; 536/23.1, 536/24.3, 25.3, 26.6

(56) References Cited

U.S. PATENT DOCUMENTS

| 3,687,808 | A | 8/1972 | Merigan, Jr. et al. ......... 195/28 |
|---|---|---|---|
| 4,910,300 | A | 3/1990 | Urdea et al. ................ 536/287 |
| 4,958,013 | A | 9/1990 | Letsinger ..................... 536/27 |
| 5,015,733 | A | 5/1991 | Smith et al. .................. 536/23 |
| 5,108,921 | A | 4/1992 | Low et al. ............... 435/240.1 |
| 5,296,350 | A | 3/1994 | Rokita et al. .................. 435/6 |
| 5,416,203 | A | 5/1995 | Letsinger ................. 536/25.34 |
| 5,466,786 | A | 11/1995 | Buhr et al. .............. 536/26.26 |
| 5,470,967 | A | 11/1995 | Huie et al. ................. 536/24.3 |
| 5,578,718 | A | 11/1996 | Cook et al. .............. 536/27.21 |

FOREIGN PATENT DOCUMENTS

| EP | 251283 | 1/1988 |
|---|---|---|
| WO | WO 86/02929 | 5/1986 |
| WO | WO 89/02931 | 4/1989 |
| WO | WO 90/10448 | 9/1990 |
| WO | WO 91/00243 | 10/1991 |
| WO | WO 91/15500 | 10/1991 |
| WO | WO 91/14696 | 11/1991 |
| WO | WO 92/05186 | 4/1993 |

OTHER PUBLICATIONS

Asseline, U. et al.,"Solid–Phase Preparation of 5'–3'–Heterobifunctional Oligodeoxyribonucleotides Using Modified Solid Supports," *Tetrahedron* 1992, 48, 1233–1254.

Asseline, U. et al., "Nucleic acid–binding molecules with high affinity and base sequence specificity: Intercalating agents covalently linked to oligodeoxynucleotides," *Proc. Natl. Acad. Sci. USA* 1984, 81, 3297–3301.

Atherton,E. et al., *The Peptides*, Gross and Meienhofer, Eds, Academic Press; New York, vol. 9:1–38, 1983.

Baker, B.F., "Decapitation of a 5'–Capped Oligoribonucleotide by o–Phenanthroline: CU(II)," *J. Am. Chem. Soc.* 1993, 115, 3378–3379.

Beaucage, S. et al., "Advances in the Synthesis of Oligonucleotides by the Phosphoramidite Approach," *Tetrahedron* 1992, 48, 2223–2311.

Bennett, C.F. et al., "Cationic Lipids Enhance Cellular Uptake and Activity of Phosphorothioate Antisense Oligonucleotides", *Molecular Pharmacology* 1991, 41, 1023–1033.

Betebenner, D.A., et al., "Hepatobiliary Delivery of Polyaminopolycarboxylate Chelates: Synthesis and Characterization of a Cholic Acid Conjugate of EDTA and Biodistribution and Imaging Studies with Its Indium–111 Chelate", *Bioconjugate Chem.* 1991, 2, 117–123.

Bischoff, R. et al., "Introduction of 5'–Terminal Functional Groups into Synthetic Oligonucleotides for Selective Immobilization," *Analy. Biochem.* 1987, 164, 336–344.

Blackburn, G. et al., "Studies in Phosphorylation. Part XXIX. The Synthesis of Dialkyl Phosphates from Monoalkyl Phosphonates: Direct Oxidative Esterification", *J. Chem. Soc.* 1966, 239–245.

Chiang, M.–Y. et al., "Antisense Oligonucleotides Inhibit Intercellular Adhesion Molecule 1 Expression by Two Distinct Mechanisms", *J. of Biol. Chem.* 1991, 266, 18162–18171.

Chollet, A., "Selective Attachment of Oligonucleotides to Interleukin–1 beta and Targeted Delivery to Cells", *Nucleosides & Nucleotides* 1990, 9, 957–966.

Cohen, J. in *Oligonucleotides: Antisense Inhibitors of Gene Expression*, CRC Press, Inc., Boca Raton, FL, pp. 1–255, 1989.

(List continued on next page.)

*Primary Examiner*—Jezia Riley
(74) *Attorney, Agent, or Firm*—Woodcock Washburn LLP

(57) ABSTRACT

Linked nucleosides having at least one functionalized nucleoside that bears a substituent such as a steroid molecule, a reporter molecule, a non-aromatic lipophilic molecule, a reporter enzyme, a peptide, a protein, a water soluble vitamin, a lipid soluble vitamin, an RNA cleaving complex, a metal chelator, a porphyrin, an alkylator, a pyrene, a hybrid photonuclease/intercalator, or an aryl azide photo-crosslinking agent exhibit increased cellular uptake and other properties. The substituent can be attached at the 2'-position of the functionalized nucleoside via a linking group. If at least a portion of the remaining liked nucleosides are 2'-deoxy-2'-fluoro, 2'-O-methoxy, 2'-O-ethoxy, 2'-O-propoxy, 2'-O-aminoalkoxy or 2'-O-allyloxy nucleosides, the substituent can be attached via a linking group at any of the 3' or the 5' positions of the nucleoside or on the heterocyclic base of the nucleoside or on the inter-nucleotide linkage linking the nucleoside to an adjacent nucleoside.

10 Claims, No Drawings

OTHER PUBLICATIONS

Corey, D. et al., "Sequence–Selective Hydrolysis of Duplex DNA by an Oligonucleotide–Directed Nuclease", *J. Am. Chem. Soc.* 1989, 111, 8523–8525.

Corey, D. et al., "Generation of a Hybrid Sequence–Specific Single–Stranded Deoxyribonuclease", *Science* 1987, 238, 1401–1403.

Damha, M. et al., "An Improved Procedure for Derivatization of Controlled–Pore Glass Beads for Solid– Phase Oligonucleotide Synthesis", *Nuc. Acids Res.* 1990, 18, 3813–3821.

Delgado, C. et al., "The Uses and Properties of PEG–Linked Proteins", *Critical Reviews in Therapeutic Drug Carrier Systems* 1992, 9, 249–304.

Dingwall, C., et al., "Protein Import Into the Cell Nucleus", *Ann. Rev. Cell Biol.* 1986, 2, 367–90.

DiZio, J. et al., "Progestin–Thenium Complexes: Metal–Labeled Steroids with High Receptor Binding Affinity, Potential Receptor–Directed Agents for Diagnostic of Therapy", *Bioconjugate Chem.* 1991, 2, 353–366.

Dreyer, G. et al., "Sequence–Specific Cleavage of Single–Stranded DNA: Oligodeoxynucleotide–EDTA.Fe(II)", *PNAS USA* 1985, 82, 968–972.

Egholm, M. et al., "Peptide Nucleic Acids (PNA). Oligonucleotide Analogues with an Achiral Peptide Backbone", *J. Am. Chem. Soc.* 1992, 114, 1895–1897.

Ferentz, A.E. and Verdine, G.L., "Disulfide Cross–Linked Oligonucleotides", *J. Am. Chem. Soc.* 1991, 113, 4000–4003.

Fidanza, J. et al., "Site–Specific Labeling of DNA Sequences Containing Phosphorothioate Diesters", *J. Am. Chem. Soc.* 1992, 114, 5509–5517.

Fidanza, J. et al., "Use of a Thiol Tether for the Site–Specific Attachment of Reporter Groups of DNA", *J. Org. Chem.* 1992, 57, 2340–2346.

Froehler, B. et al., "Synthesis of DNA via Deoxynucleoside H–Phosphonate Intermediates", *Nucleic Acids Research* 1986, 14, 5399–5407.

Gaur, R. et al., "A Simple Method for the Introduction of Thiol Group at 5'–Termini of Oligodeoxynucleotides", *Nuc. Acids Res.* 1989, 17, 4404.

Greene et al., *Protective Groups in Organic Synthesis*, 2d edition, New York, John Wiley & Sons, pp. 178–223, 1991.

Greenfield, L. et al., "Thiol–Containing Cross–Linking Agent with Enhanced Steric Hindrance", *Biodonjugate Chem.* 1990, 1, 400–410.

Guerra, F.I. et al., "Synthetic 7–Glucosyl Phospholipid as a Drug Transport System", *Tetrahedron Letters* 1987, 28, 3581–3584.

Haralambidis J., et al., "Preparation of Base–modified Nucleosides Suitable for Non–Radioactive Label Attachment and Their Incorporation Into Synthetic Oligodeoxyribonucleotides", *Nucleic Acids Research* 1987, 15, 4857–4876.

Haralambidis, J. et al., "The Solid Phase Synthesis of Oligonucleotides containing a 3'–Peptide Moiety", *Tetrahedron Letters* 1987, 28, 5199–5202.

Harris, C. et al., "New Strategy for the Synthesis of Oligodeoxynucleotides Bearing Adducts at Exocyclic Amino Sites of Purine Nucleosides", *J. Am. Chem. Soc.* 1991, 113, 4328–4329.

Iyer, R. et al., "3H–1, 2–Benzodithiole–3–one, 1,1,–Dioxide as an Improved Sulfurizing Reagent in the Solid–Phase Synthesis of Oligodeoxyribonucleoside Phosphorothioates", *J. Am. Chem. Soc.* 1990, 112, 1253–1254.

Jablonski, E. et al.,"Preparation of Oligodeoxynucleotide–Alkaline Phosphatase Conjugates and Their Use as Hybridization Probes", *Nucleic Acid Research* 1986, 14, 6115–28.

Juby, C.D., et al., "Facile Preparation of 3'Oligonucleotide–Peptide Conjugates", *Tetrahedron Letters* 1991, 32, 879–882.

Krieg, A.M., et al., "Uptake of Oligodeoxyribonucleo–tides by Lymphoid Cells Is Heterogeneous and Inducible", *Antisense Resea and Development* 1991 1, 161–171.

Lemaitre, M. et al., "Specific Antiviral Activity of a Poly(L–lysine)–Conjugated Oligodeoxyribonucleotide Sequence Complementary to Vesicular Stomatitis Virus N Protein mRNA Initiation Site", *PNAS USA* 1987, 84, 648–652.

Leonetti, J.P. et al, "Biological Activity of Oligonucleotide–Poly(L–lysine) Conjugates: Mechanism of Cell Uptake", *Bioconjugate Chem.* 1990, 1, 149–153.

Letsinger, R.L., et al., "Cholesteryl–Conjugated Oligonucleotides: Synthesis, Properties, and Activity as Inhibitors of Replication of Human Immunodeficiency Virus in Cell Culture", *Proc. Natl. Acad. Sci. USA* 1989, 86, 6553–6556.

Manoharan, M. et al., "Novel Functionalization of the Sugar Moiety of Nucleic Acids For Multiple Labeling in the Minor Groove", Tetra.Ltrs. 32:7171–7174 (1991).

Meyer, R. et al., "Efficient, Specific Cross–Linking and Cleavage of DNA by Stable, Synthetic Complementary Oligodeoxynucleotides", *J. Am. Chem. Soc.* 1989, 111, 8517–8519.

Miller, P.S., et al., "A new approach to Chemotherapy Based on Molecular Biology and Nucleic Acid Chemistry: Matagen: Masking Tape for Gene Expression", *Anti–Cancer Drug Design*, 1987, 2, 117–128.

Mirabelli, C.K., et al., "In vitro and in vivo pharmacologic activities of antisense oligonucleotides," *Anti–Cancer Drug Design*, 1991, 6, 647–661.

Mori, K., et al., "Synthesis and Properties of Novel 5'–Linked Oligos," *Nucleosides & Nucleotides*, 1989, 8, 649–657.

Nelson, P., et al., "Bifunctional Oligonucleotide Probes Synthesized Using a Novel CPG Support Are Able to Detect Single Base Pair Mutants," *Nuc. Acids Res.*, 1989, 17, 7187–7194.

Ochi, T., et al., "Synthesis and Antitumor Activity of Poly(Ethylene Glycol)s Linked to 5–Fluorouracil Via a Urethan or Urea Bond," *Drug Design and Discovery*, 1992, 9, 93–105.

Pidgeon, C. et al., Synthesis and Liposome Encapsulation of Antisense Oligonucleotide–Intercalator Conjugates, *Annals New York Academy of Sciences* pp. 593–596.

Ramirez, F. et al., "Nucleotidophospholipids: Oligonucleotide Derivatives with Membrane–Recognition Groups", *J. Am. Chem. Soc.* 1982, 104, 5483–5486.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.* 1991, 56, 4329–4333.

Shea, R. et al., "Synthesis, Hybridization Properties and Antiviral Activity of Lipid–Oligodeoxynucleotide Conjugates", *Nuc. Acids Res.* 1990, 18, 3777–3783.

Sigman, D.S., "Chemical Nucleases", *Biochemistry* 1990, 29, 9097–9105.

Sinha, N.D. et al., "The Preparation and Application of Functionalized Synthetic Oligonucleotides: III. Use of H–Phosphonate Derivatives of Protected Amino–Hexanol and Mercapto–Propanol or –Hexanol", *Nucleic Acids Res.* 1988, 16, 2659–2669.

Sluka, J. et al., "Reagents and Methods for the Solid–Phase Synthesis of Protein–EDTA for Use in Affinity Cleaving", *J. Am. Chem. Soc.* 1990, 112, 6369–6374.

Smith–Jones, P. et al., "Antibody Labeling with Copper–67 Using the Bifunctional Marcrocycle 4–((1,4,8,11–Tetraazacyclotetradec–1–yl)methyl)Benzoic Acid", *Bioconjugate Chem.* 1991, 2, 415–421.

Solomons, T.W. et al., *Organic Chemistry*, John Wiley & Sons, New York, pp. 818–819, 1980.

Sproat, B. et al., "The Synthesis of Protected 5'-Mercapto-2', 5'-Dideoxyribonucleoside-3'-O-Phosphoramidites; Uses of 5'-Mercapto-Oligodeoxyribonucleotides", *Nucleic Acids Res.* 1987, 15, 4837–4848.

Stein, C. et al., "Antisense Oligonucleotides as Therapeutic Agents—Is the Bullet Really Magical?" *Science* 1993, 261, 1004–1012.

Telser, J. et al., "Synthesis and Characterization of DNA Oligomers and Duplexes Containing Covalently Attached Molecular Labels: Comparison of Biotin, Fluorescin, and Pyrene Labels by Thermodynamic and Optical Spectroscopic Measurements", *J. Am. Chem. Soc.* 1989, 111, 6966–6976.

Tseng, B. et al.,"Antisense Oligonucleotide Technology in the Development of Cancer Therapeutics", *Cancer Gene Therapy* 1994, 1(1), 65–71.

Uhlmann, E. and A. Peyman, "Antisense Oligonucleotides: A New Therapeutic Principle," *Chem. Rev.* 1990, 90, 543–584.

Vasseur, J. et al., "Oligonucleosides: Synthesis of a Novel Methylhydroxylamine–Linked Nucleosides Dimer and its Incorporation into Antisense Sequences", *J. Am. Chem. Soc.* 1992, 114, 4006–4007.

Veber, D. et al., "Isonicotinyloxycarbonyl, a Novel Amino Protecting Group for Peptide Synthesis", *J. Org. Chem.* 1977, 42, 3286–3288.

Wagner, D. et al., "Preparation and Synthetic Utility of Some Organotin Derivatives of Nucleosides", *J. Org. Chem.* 1974, 39, 24–30.

Wychowski, C. et al., "The Intranuclear Location of Simian Virus 40 Polypeptides VP2 and VP3 Depends on a Specific Amino Acid Sequence", *J. Virol.* 1987, 61, 3862–3869.

Yamana, K. et al., Synthesis of Oligonucleotide Derivatives with Pyrene Group at Sugar Fragment, *Tetrahedron Lett.* 1991, 32, 6347–6350.

Yamana, K. et al., "Synthesis and Interactive Properties of an Oligonucleotide with Anthraquinone at the Sugar Fragment", *Bioconjugate Chem.* 1990, 1, 319–324.

Yoneda, Y. et al., "Synthetic Peptides Containing a Region of SV40 Large T–Antigen Involved in Nuclear Localizatiion Direct the Transport of Proteins Into the Nucleus", *Experimental Cell Research* 1987, 170, 439.

Zhang, Z. and McCormick,"Uptake of N–(4'–pyridoxyl)amines and Release of Amines by Renal Cells: A Model for Transporter–Enhanced Delivery of Bioactive Compounds", *PNAS USA* 1991, 88, 10407–10410.

Zuckermann, R. et al., "Site–Selective Cleavage of RNA by a Hybrid Enzyme", *J. Am. Chem. Soc.* 1988, 110, 1614–1615.

Zuckermann et al., "Efficient Methods for Attachment of Thiol Specific Probes to The 3'–Ends of Synthetic Oligodeoxyribonucleotides", *Nucleic Acids Research* 1987, 15, 5305–5320.

Englisch, U. et al., "Chemically Modified Oligonucleotides as Probes and Inhibitors",*Angew. Chem. Int. Ed. Eng.*, 1991, 30, 613–629.

Manoharan, et al., "Novel Functionalization of the Sugar Moiety of Nucleic Acids for Multiple Labeling in the Minor Grove," *Tetrahedron Letters*, 1991, 32, 7171.

Goodchild, "Conjugates of Oligonucleotides and Modified Oligonucleotides: A Review of Their Synthesis and Properties," *Bioconjugate Chemistry*, 1990, 1, 165.

Monoharan, et al., "Chemical Modifications to Improve Uptake and Bioavailability of Antisense Oligonculeotides," *Database Embase Elsevier Science Publishers*, 1992, 660, 306 (abstract).

Caruthers, Synthesis of oligonucleotides and oligonucleotide analogues, Antisense inhibitors of gene expression, J.S. Cohen (ed.), *CRC Press, Boca Raton, FL.*, 1989, 7–24.

Mitchell, et al., "Boron trifluoride–menthanol complex as a non–depurinating detritylating agent in DNA synthesis," *Nucleic Acids Research*, 1990, 18(17).

Schwartz, et al., "The DNA bending by acetylaminofluorene residues and by apurinic sites," *J. Mol. Biol.*, 1989, 207, 445–450.

Harallambidis, et al., "The solid phase synthesis of oligonucleotides containing a 3'peptide moiety," *Tett. Ltrs.*, 1987, 28, 5199–5202.

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Novel Sequence

<400> SEQUENCE: 1
ttgcttccat cttcctcgtc                                              20

<210> SEQ ID NO 2
<211> LENGTH: 17
<212> TYPE: DNA
<213> ORGANISM: Artificial Sequence
<220> FEATURE:
<223> OTHER INFORMATION: Novel Sequence

<400> SEQUENCE: 2
ctgtctccat cttcact                                                 17

<210> SEQ ID NO 3
<211> LENGTH: 20
<212> TYPE: DNA
<213> ORGANISM: Artificial Sequence
<220> FEATURE:
<223> OTHER INFORMATION: Novel Sequence

<400> SEQUENCE: 3
ctgtctccat cctcttcact                                              20

<210> SEQ ID NO 4
<211> LENGTH: 18
<212> TYPE: DNA
<213> ORGANISM: Artificial Sequence
<220> FEATURE:
<223> OTHER INFORMATION: Novel Sequence

<400> SEQUENCE: 4
tgggagccat agcgaggc                                                18

<210> SEQ ID NO 5
<211> LENGTH: 12
<212> TYPE: RNA
<213> ORGANISM: Artificial Sequence
```

```
-continued

<220> FEATURE:
<223> OTHER INFORMATION: Novel Sequence

<400> SEQUENCE: 5
cccaggcuca ga                                                              12

<210> SEQ ID NO 6
<211> LENGTH: 12
<212> TYPE: RNA
<213> ORGANISM: Artificial Sequence
<220> FEATURE:
<223> OTHER INFORMATION: Novel Sequence

<400> SEQUENCE: 6
gagcucccag gc                                                              12

<210> SEQ ID NO 7
<211> LENGTH: 11
<212> TYPE: DNA
<213> ORGANISM: Artificial Sequence
<220> FEATURE:
<223> OTHER INFORMATION: Novel Sequence

<400> SEQUENCE: 7
ggctgactgc g                                                               11

<210> SEQ ID NO 8
<211> LENGTH: 12
<212> TYPE: RNA
<213> ORGANISM: Artificial Sequence
<220> FEATURE:
<223> OTHER INFORMATION: Novel Sequence

<400> SEQUENCE: 8
ccaagccuca ga                                                              12

<210> SEQ ID NO 9
<211> LENGTH: 12
<212> TYPE: DNA
<213> ORGANISM: Artificial Sequence
<220> FEATURE:
<223> OTHER INFORMATION: Novel Sequence

<400> SEQUENCE: 9
ccaggcucag at                                                              12

<210> SEQ ID NO 10
<211> LENGTH: 16
<212> TYPE: DNA
<213> ORGANISM: Artificial Sequence
<220> FEATURE:
<223> OTHER INFORMATION: Novel Sequence

<400> SEQUENCE: 10
tccaggtgtc cgcatc                                                          16

<210> SEQ ID NO 11
<211> LENGTH: 17
<212> TYPE: DNA
<213> ORGANISM: Artificial Sequence
<220> FEATURE:
<223> OTHER INFORMATION: Novel Sequence

<400> SEQUENCE: 11
ggaccggaag gtacgag                                                         17
```

<210> SEQ ID NO 12
<211> LENGTH: 17
<212> TYPE: DNA
<213> ORGANISM: Artificial Sequence
<220> FEATURE:
<223> OTHER INFORMATION: Novel Sequence

<400> SEQUENCE: 12
cctggccttc catgctc                                                  17

<210> SEQ ID NO 13
<211> LENGTH: 17
<212> TYPE: RNA
<213> ORGANISM: Artificial Sequence
<220> FEATURE:
<223> OTHER INFORMATION: Novel Sequence

<400> SEQUENCE: 13
ccuggccuuc caugcuc                                                  17

<210> SEQ ID NO 14
<211> LENGTH: 12
<212> TYPE: RNA
<213> ORGANISM: Artificial Sequence
<220> FEATURE:
<223> OTHER INFORMATION: Novel Sequence

<400> SEQUENCE: 14
caugcugcag cc                                                       12

<210> SEQ ID NO 15
<211> LENGTH: 18
<212> TYPE: DNA
<213> ORGANISM: Artificial Sequence
<220> FEATURE:
<223> OTHER INFORMATION: Novel Sequence

<400> SEQUENCE: 15
tgggagccgt agcgaggc                                                 18

<210> SEQ ID NO 16
<211> LENGTH: 21
<212> TYPE: RNA
<213> ORGANISM: Artificial Sequence
<220> FEATURE:
<223> OTHER INFORMATION: Novel Sequence

<400> SEQUENCE: 16
ggcgucucca ggggaucuga c                                             21

<210> SEQ ID NO 17
<211> LENGTH: 20
<212> TYPE: DNA
<213> ORGANISM: Artificial Sequence
<220> FEATURE:
<223> OTHER INFORMATION: Novel Sequence

<400> SEQUENCE: 17
tctgagtagc agaggagctc                                               20

<210> SEQ ID NO 18
<211> LENGTH: 31
<212> TYPE: RNA
<213> ORGANISM: Artificial Sequence
<220> FEATURE:
<223> OTHER INFORMATION: Novel Sequence -continued

```
<400> SEQUENCE: 18
ggccagaucu gagccuggga gcucuguggc c                                    31
```

DERIVATIZED OLIGONUCLEOTIDES HAVING IMPROVED UPTAKE AND OTHER PROPERTIES

CROSS REFERENCE TO RELATED APPLICATIONS

This application is a divisional of application Ser. No. 09/633,659, filed on Aug. 7, 2000, now U.S. Pat. No. 6,395,492, which is a divisional of application Ser. No. 08/211,882, filed Apr. 22, 1994, now U.S. Pat. No. 6,153,737, which is a continuation-in-part of PCT/US92/09196, filed Oct. 23, 1992. The disclosure of each of the foregoing is hereby incorporated by reference.

FIELD OF THE INVENTION

This application is directed to sequence specific oligonucleotides that include functionalized nucleosides having substituents such as steroids, reporter molecules, reporter enzymes, non-aromatic lipophilic molecules, peptides, or proteins attached via linking groups.

BACKGROUND OF THE INVENTION

Messenger RNA (mRNA) directs protein synthesis. Antisense methodology is the complementary hybridization of relatively short oligonucleotides to mRNA or DNA such that the normal, essential functions of these intracellular nucleic acids are disrupted. Hybridization is the sequence-specific hydrogen bonding of oligonucleotides to RNA or single-stranded DNA via complementary Watson-Crick base pairs.

The naturally occurring events that provide the disruption of the nucleic acid function, discussed by Cohen in *Oligonucleotides: Antisense Inhibitors of Gene Expression*, CRC Press, Inc., Boca Raton, Fla. (1989), are thought to be of two types. The first, hybridization arrest, denotes a terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (see, e.g., Miller, et al., *Anti-Cancer Drug Design* 1987, 2, 117) and α-anomer oligonucleotides, the two most extensively studied antisense agents, are thought to disrupt nucleic acid function by hybridization arrest.

The second type of terminating event for antisense oligonucleotides involves the enzymatic cleavage of targeted RNA by intracellular RNase H. A 2'-deoxyribofuranosyl oligonucleotide or oligonucleotide analog hybridizes with the targeted RNA to form a duplex that activates the RNase H enzyme to cleave the RNA strand, thus destroying the normal function of the RNA. Phosphorothioate oligonucleotides provide the most prominent example of antisense agents that operate by this type of antisense terminating event.

Considerable research is being directed to the application of oligonucleotides and oligonucleotide analogs as antisense agents for diagnostics, research reagents, and therapeutics. At least for therapeutic purposes, the antisense oligonucleotides and oligonucleotide analogs must be transported across cell membranes or taken up by cells to express activity. One method for increasing membrane or cellular transport is by the attachment of a pendant lipophilic group.

Ramirez, et al., *J. Am. Chem. Soc.* 1982, 104:, 5483, introduced the phospholipid group 5'-O-(1,2-di-O-myristoyl-sn-glycero-3-phosphoryl) into the dimer TpT independently at the 3' and 5' positions. Subsequently Shea, et al., *Nuc. Acids Res.* 1990, 18, 3777, disclosed oligonucleotides having a 1,2-di-O-hexyldecyl-rac-glycerol group linked to a 5'-phosphate on the 5'-terminus of the oligonucleotide. Certain of the Shea, et. al. authors disclosed these and other compounds in patent application PCT/US90/01002. Another glucosyl phospholipid was disclosed by Guerra, et al., *Tetrahedron Letters* 1987, 28, 3581.

In other work, a cholesteryl group was attached to the inter-nucleotide linkage between the first and second nucleotides (from the 3' terminus) of an oligonucleotide. This work is disclosed in U.S. Pat. No. 4,958,013 and by Letsinger, et al., *Proc. Natl. Acad. Sci. USA* 1989, 86, 6553. The aromatic intercalating agent anthraquinone was attached to the 2' position of a sugar fragment of an oligonucleotide as reported by Yamana, et al., *Bioconjugate Chem.* 1990, 1, 319.

Lemairte, et al., *Proc. Natl. Acad. Sci. USA* 1986, 84, 648 and Leonetti, et al., *Bioconjugate Chem.* 1990, 1, 149, disclose modifying the 3' terminus of an oligonucleotide to include a 3'-terminal ribose sugar moiety. Poly(L-lysine) was linked to the oligonucleotide via periodate oxidation of this terminal ribose followed by reduction and coupling through a N-morpholine ring. Oligonucleotide-poly(L-lysine) conjugates are described in European Patent application 87109348.0, wherein the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide, as described by Corey, et al., *Science* 1987, 238, 1401; Zuckermann, et al., *J. Am. Chem. Soc.* 1988, 110, 1614; and Corey, et al., *J. Am. Chem. Soc.* 1989, 111, 8524.

Nelson, et al., *Nuc. Acids Res.* 1989, 17, 7187 describe a linking reagent for attaching biotin to the 3'-terminus of an oligonucleotide. This reagent, N-Fmoc-O-DMT-3-amino-1, 2-propanediol, is commercially available from Clontech Laboratories (Palo Alto, Calif.) under the name 3'-Amine on and from Glen Research Corporation (Sterling, Va.) under the name 3'-Amino-Modifier. This reagent was also utilized to link a peptide to an oligonucleotide, as reported by Judy, et al., *Tetrahedron Letters* 1992, 32, 879. A similar commercial reagent (actually a series of linkers having various lengths of polymethylene connectors) for linking to the 5'-terminus of an oligonucleotide is 5'-Amino-Modifier C6, also from Glen Research Corporation. These compounds or similar ones were utilized by Krieg, et al., *Antisense Research and Development* 1991, 1, 161 to link fluorescein to the 5'-terminus of an oligonucleotide. Other compounds of interest have also been linked to the 3'-terminus of an oligonucleotide. Asseline, et al., *Proc. Natl. Acad. Sci. USA* 1984, 81, 3297 described linking acridine on the 3'-terminal phosphate group of an poly (Tp) oligonucleotide via a polymethylene linkage. Haralambidis, et al., *Tetrahedron Letters* 1987, 28, 5199 reported building a peptide on a solid state support and then linking an oligonucleotide to that peptide via the 3'hydroxyl group of the 3'terminal nucleotide of the oligonucleotide. Chollet, *Nucleosides & Nucleotides* 1990, 9, 957 attached an Aminolink 2 (Applied Biosystems, Foster City, Calif.) to the 5' terminal phosphate of an oligonucleotide. They then used the bifunctional linking group SMPB (Pierce Chemical Co., Rockford, Ill.) to link an interleukin protein to the oligonucleotide.

An EDTA iron complex has been linked to the 5 position of a pyrimidine nucleoside as reported by Dreyer, et al., *Proc. Natl. Acad. Sci. USA* 1985, 82, 968. Fluorescein has been linked to an oligonucleotide in the same manner, as reported by Haralambidis, et al., *Nucleic Acid Research* 1987, 15, 4857 and biotin in the same manner as described in PCT application PCT/US/02198. Fluorescein, biotin and pyrene were also linked in the same manner as reported by Telser, et al., *J. Am. Chem. Soc.* 1989, 111, 6966. A commercial reagent, Amino-Modifier-dT from Glen Research Corporation, can be utilized to introduce pyrimidine nucleotides bearing similar linking groups into oligonucleotides.

Cholic acid linked to EDTA for use in radioscintigraphic imaging studies was reported by Betebenner, et al., *Bioconjugate Chem.* 1991, 2, 117; however, it is not known to link cholic acid to nucleosides, nucleotides or oligonucleotides.

OBJECTS OF THE INVENTION

It is an object of this invention to provide sequence-specific oligonucleotides having improved transfer across cellular membranes.

It is a further object of this invention to provide improvements in research and diagnostic methods and materials for assaying bodily states in animals, especially disease states.

It is an additional object of this invention to provide therapeutic and research materials having improved transfer and uptake properties for the treatment of diseases through modulation of the activity of DNA or RNA.

BRIEF DESCRIPTION OF THE INVENTION

In accordance with these and other objects evident from this specification, there are provided compounds that comprise a plurality of linked nucleosides wherein at least one of the nucleosides is functionalized at the 2'-position with a substituent such as, for example, a steroid molecule, a reporter molecule, a non-aromatic lipophilic molecule, a reporter enzyme, a peptide, a protein, a water soluble vitamin, a lipid soluble vitamin, an RNA cleaving complex, a metal chelator, a porphyrin, an alkylator, a hybrid photonuclease/intercalator, a pyrene, or an aryl azide photo-crosslinking agent. Preferably, the substituent is connected to 2'-position using an intervening linking group.

In certain preferred embodiments of the invention, the substituents comprise a steroid molecule, biotin, a reporter enzyme or a fluorescein dye molecule. In these embodiments, the steroid molecule is selected from the group consisting, of cholic acid, deoxycholic acid, dehydrocholic acid, cortisone, testosterone, cholesterol and digoxigenin with the most preferred steroid molecule being cholic acid. Preferred reporter enzymes include horseradish peroxidase and alkaline phosphatase.

In further preferred embodiments, the non-aromatic lipophilic molecule attached to the 2'-position comprises an alicyclic hydrocarbon, saturated or unsaturated fatty acid, wax, terpenoid, or polyalicyclic hydrocarbon, including adamantane and buck-minsterfullerenes. Waxes according to the invention include monohydric alcohol esters of fatty acids and fatty diamides. Buckminsterfullerenes include soccer ball-shaped, cage molecules comprising varying numbers of covalently bound carbon atoms. Terpenoids include the $C_{10}$ terpenes, $C_{20}$ sesquiterpenes, $C_{30}$ diterpenes including vitamin A (retinol), retinoic acid, retinal and dehydroretinol, $C_{30}$ triterpenes, $C_{40}$ tetraterpenes and other higher polyterpenoids.

In other preferred embodiments, peptides or proteins attached to the 2'-position comprise sequence-specific peptides and sequence-specific proteins, including phosphatases, peroxidases and nucleases.

Preferred linking molecules of the invention comprise Ω-aminoalkoxy linkers, Ω-aminoalkylamino linkers, heterobifunctional linkers or homobifunctional linkers. A particularly preferred linking molecule of the invention is a 5-aminopentoxy group.

In preferred embodiments of the invention at least a portion of the linked nucleosides are 2'-deoxy-2'-fluoro, 2'-methoxy, 2'-ethoxy, 2'-propoxy, 2'-aminoalkoxy or 2'-allyloxy nucleosides. In other preferred embodiments of the invention the linked nucleosides are linked with phosphorothioate linking groups.

The invention also provides compounds that have a plurality of linked nucleosides. In preferred embodiments, at least one of the nucleosides is: (1) a 2'-functionalized nucleoside having cholic acid linked to its 2'-position; (2) a heterocyclic base functionalized nucleoside having cholic acid linked to its heterocyclic base; (3) a 5' terminal nucleoside having cholic acid linked to its 5'-position; (4) a 3' terminal nucleoside having cholic acid linked to its 3'-position; or (5) an inter-strand nucleoside having cholic acid linked to an inter-stand linkage linking said inter-strand nucleoside to an adjacent nucleoside.

In certain embodiments of the invention having linked nucleosides, at least one linked nucleosides bears a 2'-deoxy'-2'-fluoro, 2'-O—$C_1$–$C_{20}$-alkyl, 2'-O—$C_2$–$C_{20}$-alkenyl, 2'-O—$C_2$–$C_{20}$-alkynyl, 2'-S—$C_1$–$C_{20}$-alkyl, 2'-S—$C_2$–$C_{20}$-alkenyl, 2'-S—$C_2$–$C_{20}$-alkynyl, 2'-NH—$C_1$–$C_{20}$-alkyl, 2'-NH—$C_2$–$C_{20}$-alkenyl, or 2'-NH—$C_2$–$C_{20}$-alkynyl substituent.

Further in accordance with the invention there is provided a method of increasing cellular uptake of a compound having a plurality of linked nucleosides that includes contacting an organism with a compound where the compound includes at least one nucleoside functionalized at the 2'-position with a steroid molecule, a reporter molecule, a non-aromatic lipophilic molecule, a reporter enzyme, a peptide, a protein, a water soluble vitamin, and a lipid soluble vitamin. The compound can be included in a composition that further includes an inert carrier for the compound.

The invention also provides a method for enhancing the binding affinity and/or stability of an antisense oligonucleotide comprising functionalizing the oligonucleotide with a steroid molecule, a reporter molecule, a non-aromatic lipophilic molecule, a reporter enzyme, a peptide, a protein, a water soluble vitamin, and a lipid soluble vitamin.

DETAILED DESCRIPTION OF THE INVENTION

Antisense therapeutics can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to antisense therapeutics and/or prophylactics. Seemingly diverse organisms such as bacteria, yeast, protozoa, algae, all plant and all higher animal forms, including warm-blooded animals, can be treated by antisense therapy. Further, since each of the cells of multicellular eukaryotes also includes both DNA-RNA transcription and RNA-protein translation as an integral part of its cellular activity, antisense therapeutics and/or diagnostics can also be practiced on such cellular populations. Furthermore, many of the organelles, e.g., mitochondria and chloroplasts, of eukaryotic cells also include transcription and translation mechanisms. As such, single cells, cellular populations or organelles can also be included within the definition of organisms that are capable of being treated with antisense therapeutics or diagnostics. As used herein, therapeutics is meant to include both the eradication of a disease state, killing of an organism, e.g., bacterial, protozoan or other infection, or control of erratic or harmful cellular growth or expression.

While we do not wish to be bound by any particular theory, it is believed that the presence of many nuclear proteins in the nucleus is due to their selective entry through the nuclear envelope rather than to their selective retention within the nucleus after entry. By this mechanism, the nucleus is able to selectively take up certain proteins and not others. The uptake is based upon the sequence of the peptide or protein, which provides a selective signal sequence that allows accumulation of the peptide or protein in the nucleus. One such peptide signal sequence is found as part of the SV40 large T-antigen. See, e.g., Dingwell, et al. *Ann. Rev. Cell Bio.* 1986, 2, 367; Yoneda, et al., *Experimental Cell Research* 1987, 170, 439; and Wychowski, et al., *J. Virol.* 1986, 61, 3862.

According to the present invention a substituent such as a steroid molecule, a reporter molecule, a non-aromatic lipophilic molecule, a reporter enzyme, a peptide, a protein, a water soluble vitamin, a lipid soluble vitamin, an RNA cleaving complex, a metal chelator, a porphyrin, an alkylator, a hybrid photonuclease/intercalator, or an aryl azide photo-crosslinking agent is attached to at least one nucleoside in an antisense diagnostic or therapeutic agent to assist in the transfer of the antisense therapeutic or diagnostic agent across cellular membranes. Such antisense diagnostic or therapeutic agent is formed from a plurality of linked nucleosides of a sequence that is "antisense" to a region of an RNA or DNA that is of interest. Thus, one or more nucleoside of the linked nucleosides are "functionalized" to include a substituent linked to the nucleoside via a linking group. For the purposes of identification, such functionalized nucleosides can be characterized as substituent-bearing (e.g., steroid-bearing) nucleosides. Linked nucleosides having at least one functionalized nucleoside within their sequence demonstrate enhanced antisense activity when compared to linked nucleoside that do not contain functionalized nucleoside. These "functionalized" linked nucleosides further demonstrate increased transfer across cellular membranes.

For the purposes of this invention. the terms "reporter molecule" and "reporter enzyme" include molecules or enzymes having physical or chemical properties that allow them to be identified in gels, fluids, whole cellular systems, broken cellular systems, and the like utilizing physical properties such as spectroscopy, radioactivity, colorimetric assays, fluorescence, and specific binding. Steroids include chemical compounds that contain a perhydro-1,2-cyclopentanophenanthrene ring system. Proteins and peptides are utilized in their usual sense as polymers of amino acids. Normally peptides are amino acid polymers that contain a fewer amino acid monomers per unit molecule than proteins. Non-aromatic lipophilic molecules include fatty acids, esters, alcohols and other lipid molecules, as well as synthetic cage structures such as adamantane and buckminsterfullerenes that do not include aromatic rings within their structure.

Particularly useful as steroid molecules are the bile acids, including cholic acid, deoxycholic acid and dehydrocholic acid. Other useful steroids are cortisone, digoxigenin, testosterone, cholesterol and cationic steroids such as cortisone having a trimethylaminomethyl hydrazide group attached via a double bond at the 3 position of the cortisone rings. Particularly useful reporter molecules are biotin and fluorescein dyes. Particularly useful non-aromatic lipophilic molecules are alicyclic hydrocarbons, saturated and unsaturated fatty-acids, waxes, terpenes, and polyalicyclic hydrocarbons, including adamantane and buckminsterfullerenes. Particularly useful reporter enzymes are alkaline phosphatase and horseradish peroxidase. Particularly useful peptides and proteins are sequence-specific peptides and proteins, including phosphodiesterase, peroxidase, phosphatase, and nuclease proteins. Such peptides and proteins include SV40 peptide, RNase A, RNase H and Staphylococcal nuclease. Particularly useful terpenoids are vitamin A, retinoic acid, retinal, and dehydroretinol.

Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobamide coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), Retinol-binding protein (RBP), and cellular retinol-binding protein (CRBP). These proteins, which have been found in various parts of the human body, have molecular weights of approximately 15 kD. They have specific interactions with compounds of vitamin-A family, especially, retinoic acid and retinol.

The vitamin A family of compounds can be attached to oligonucleotides via acid or alcohol functionalities found in the various family members. For example, conjugation of an N-hydroxy succinimide ester of an acid moiety of retinoic acid to an amine function on a linker pendant to an oligonucleotide resulted in linkage of vitamin A compound to the oligonucleotide via an amide bond. Also, retinol was converted to its phosphoramidite, which is useful for 5' conjugation.

α-Tocopherol (vitamin E) and the other tocopherols (beta through zeta) can be conjugated to oligonucleotides to enhance uptake because of their lipophilic character. Also, the lipophilic vitamin, vitamin D, and its ergosterol precursors can be conjugated to oligonucleotides through their hydroxyl groups by first activating the hydroxyls groups to, for example, hemisuccinate esters. Conjugation then is effected to an aminolinker pendant from the oligonucleotide. Other vitamins that can be conjugated to oligonucleotide aminolinkers through hydroxyl groups on the vitamins include thiamine, riboflavin, pyridoxine, pyridoxamine, pyridoxal, deoxypyridoxine. Lipid soluble vitamin K's and related quinone-containing compounds can be conjugated via carbonyl groups on the quinone ring. The phytol moiety of vitamin K may also serve to enhance bind of the oligonucleotides to cells.

Pyridoxal (vitamin $B_6$) has specific $B_6$-binding proteins. The role of these proteins in pyridoxal transport has been studied by Zhang and McCormick, *Proc. Natl. Acad. Sci. USA*, 1991 88, 10407. Zhang and McCormick also have shown that a series of N-(4'-pyridoxyl)amines, in which several synthetic amines were conjugated at the 4'-position of pyridoxal, are able to enter cells by a process facilitated by the B6 transporter. They also demonstrated the release of these synthetic amines within the cell. Other pyridoxal family members include pyridoxine, pyridoxamine, pyridoxal phosphate, and pyridoxic acid. Pyridoxic acid, niacin, pantothenic acid, biotin, folic acid and ascorbic acid can be conjugated to oligonucleotides using N-hydroxysuccinimide esters that are reactive with aminolinkers located on the oligonucleotide, as described above for retinoic acid.

Other groups for modifying antisense properties include RNA cleaving complexes, pyrenes, metal chelators, porphyrins, alkylators, hybrid intercalator/ligands and photo-crosslinking agents. RNA cleavers include o-phenanthroline/Cu complexes and Ru(bipyridine)$_3^{2+}$ complexes. The Ru(bpy)$_3^{2+}$ complexes interact with nucleic acids and cleave nucleic acids photochemically. Metal chelators are include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

Hybrid intercalator/ligands include the photonuclease/intercalator ligand 6-[[[9-[[6-(4-nitro-benzamido)hexyl]amino]acridin-4-yl]carbonyl]amino]hexanoyl-pentafluorophenyl ester. This compound has two noteworthy features: an acridine moiety that is an intercalator and a p-nitro benzamido group that is a photonuclease.

Photo-crosslinking agents include aryl azides such as, for example, N-hydroxysucciniimidyl-4-azidobenzoate (HSAB) and N-succinimidyl-6(-4'-azido-2'-nitrophenyl-amino)hexanoate (SANPAH). Aryl azides conjugated to oligonucleotides effect crosslinking with nucleic acids and proteins upon irradiation, They also crosslink with carrier proteins (such as KLH or BSA), raising antibody against the oligonucleotides.

A variety of linking groups can be used to connect the substituents of the invention to nucleosides, nucleotides, and/or oligonucleotides. Certain linking groups, such as Ω-aminoalkoxy moieties and Ω-aminoalkylamino moieties, are particularly useful for linking steroid molecules or reporter molecules to the 2'-position of a nucleoside. Many linking groups are commercially available, including heterobifunctional and homobifunctional linking moieties available from the Pierce Co. (Rockford, Ill.). Heterobifunctional and homobifunctional linking moieties are particularly useful in conjunction with the Ω-aminoalkoxy and Ω-aminoalkylamino moieties to form extended linkers that connect peptides and proteins to nucleosides. Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.). A nucleotide analog bearing a linking group pre-attached to the nucleoside is commercially available from Glen Research Corporation under the tradename "Amino-Modifier-dT." This nucleoside-linking group reagent, a uridine derivative having an [N(7-trifluoroacetylaminoheptyl)3-acrylamido] substituent group at the 5 position of the pyrimidine ring, is synthesized generally according to Jablonski, et al., *Nucleic Acid Research* 1986, 14, 6115. It is intended that the nucleoside analogs of the invention include adenine nucleosides functionalized with linkers on their N6 purine amino groups, guanine nucleosides functionalized with linkers at their exocyclic N2 purine amino groups, and cytosine nucleosides functionalized with linkers on either their N4 pyrimidine amino groups or 5 pyrimidine positions.

Sequence-specific linked nucleosides of the invention are assembled on a suitable DNA synthesizer utilizing either standard nucleotide precursors or nucleotide precursors that already bear linking moieties. Once synthesis of the sequence-specific linked nucleosides is complete, a substituent can be reacted with the linking moiety. Thus, the invention preferably first builds a desired linked nucleoside sequence by known techniques on a DNA synthesizer. One or more of the linked nucleosides are then functionalized or derivatized with a selected substituent.

PCT/US91/00243, application Ser. No. 463,358, and application Ser. No. 566,977, which are incorporated herein by reference, disclose that incorporation of, for example, a 2'-O-methyl, 2'-O-ethyl, 2'-O-propyl, 2'-O-alkyl, 2'-O-aminoalkyl or 2'-deoxy-2'-fluoro groups on the nucleosides of an oligonucleotide enhance the hybridization properties of the oligonucleotide. These applications also disclose that oligonucleotides containing phosphorothioate backbones have enhanced nuclease stability. The functionalized, linked nucleosides of the invention can be augmented to further include either or both a phosphorothioate backbone or a 2'-O—$C_1$–$C_{20}$-alkyl (e.g., 2'-O-methyl, 2'-O-ethyl, 2'-O-propyl), 2'-O—$C_2$–$C_{20}$-alkenyl (e.g., 2'-O-allyl), 2'-O—$C_2$–$C_{20}$-alkynyl, 2'-S—$C_1$–$C_{20}$-alkyl, 2'-S—$C_2$–$C_{20}$-alkenyl, 2'-S—$C_2$–$C_{20}$-alkynyl, 2'-NH—$C_1$–$C_{20}$-alkyl (2'-O-aminoalkyl), 2'-NH—$C_2$–$C_{20}$-alkenyl, 2'-NH—$C_2$–$C_{20}$-alkynyl or 2'-deoxy-2'-fluoro group. See, e.g., application Ser. No. 918,362, filed Jul. 23, 1992, which is incorporated by reference.

An oligonucleotide possessing an amino group at its 5'-terminus is prepared using a DNA synthesizer and then is reacted with an active ester derivative of the substituent of the invention (e.g., cholic acid). Active ester derivatives are well known to those skilled in the art. Representative active esters include N-hydrosuccinimide esters, tetrafluorophenolic esters, pentafluorophenolic esters and pentachlorophenolic esters. For cholic acid, the reaction of the amino group and the active ester produces an oligonucleotide in which cholic acid is attached to the 5'-position through a linking group. The amino group at the 5'-terminus can be prepared conveniently utilizing the above-noted 5'-Amino-Modifier C6 reagent.

Cholic acid can be attached to a 3'-terminal amino group by reacting a 3'-amino modified controlled pore glass (sold by Clontech Laboratories Inc., Palo Alto, Calif.), with a cholic acid active ester.

Cholic acid can be attached to both ends of a linked nucleoside sequence by reacting a 3',5'-diamino sequence with the cholic acid active ester. The required oligonucleoside sequence is synthesized utilizing the 3'-Amino-Modifier and the 5'-Amino-Modifier C6 (or Aminolink-2) reagents noted above or by utilizing the above-noted 3'-amino modified controlled pore glass reagent in combination with the 5'-Amino-Modifier C2 (or Aminolink-2) reagents.

In even further embodiments of the invention, an oligonucleoside sequence bearing an aminolinker at the 2'-position of one or more selected nucleosides is prepared using a suitably functionalized nucleotide such as, for example, 5'-dimethoxytrityl-2'-O-(ε-phthalimidylaminopentyl)-2'-deoxyadenosine-3'-N,N-diisopropyl-cyanoethoxy phosphoramidite. See, e.g., Manoharan, et al., *Tetrahedron Letters*, 1991, 34, 7171 and above-referenced application Ser. Nos. PCT/US91/00243, 566,977, and 463,358. The nucleotide or nucleotides are attached to cholic acid or another substituent using an active ester or a thioisocyanate thereof. This approach allows the introduction of a large number of functional groups into an linked nucleoside sequence. Indeed each of the nucleosides can be so substituted.

In further functionalized nucleoside sequences of the invention, the heterocyclic base of one or more nucleosides is linked to a steroid molecule, a reporter molecule, a non-aromatic lipophilic molecule, a reporter enzyme, a peptide, a protein, a water soluble vitamin, a lipid soluble vitamin, an RNA cleaving complex, a metal chelator, a porphyrin, an alkylator, a hybrid photonuclease/intercalator, or an aryl azide photo-crosslinking agent. Utilizing 5'-O-dimethoxytrityl-5-[N(7-trifluoroacetylaminoheptyl)-3-acryl-amido]-2'-deoxyuridine 3'-O-(methyl N,N-diisopropyl)phosphoramide, as described by Jablonski, et al. above (also commercially available from Glen Research), the desired nucleoside, functionalized to incorporate a linking group on its heterocyclic base, is incorporated into the linked nucleoside sequence using a DNA synthesizer.

Conjugation (linking) of reporter enzymes, peptides, and proteins to linked nucleosides is achieved by conjugation of the enzyme, peptide or protein to the above-described amino linking group on the nucleoside. This can be effected in several ways. A peptide- or protein-functionalized nucleoside of the invention can be prepared by conjugation of the peptide or protein to the nucleoside using EDC/sulfo-NHS (i.e., 1-ethyl-3(3-dimethylaminopropylcarbodiimide/N-hydroxysulfosuccinimide) to conjugate the carboxyl end of the reporter enzyme, peptide, or protein with the amino function of the linking group on the nucleotide. Further, a linked nucleoside sequence of the invention can be prepared using EDC/sulfo-NHS to conjugate a carboxyl group of an aspartic or glutamic acid residue in the reporter enzyme, peptide or protein to the amino function of a linked nucleoside sequence.

Preferably a reporter enzyme-, peptide-, protein-functionalized linked nucleoside sequence can be prepared by conjugation of the reporter enzyme, peptide or protein to the nucleoside sequence via a heterobifunctional linker such as m-maleimidobenzoyl-N-hydroxysulfosuccinimide ester (MBS) or succinimidyl 4-(N-maleimidomethyl) cyclohexane-1-carboxylate (SMCC) to link a thiol function on the reporter enzyme, peptide or protein to the amino function of the linking group on nucleoside sequence. By this mechanism, an oligonucleoside-maleimide conjugate is formed by reaction of the amino group of the linker on the linked nucleosides with the MBS or SMCC maleimide linker. The conjugate is then reacted with peptides or proteins having free sulfhydryl groups.

In a second preferred method, a reporter enzyme-, peptide-, protein-functionalized linked nucleoside sequence can be prepared by conjugation of the peptide or protein to the sequence using a homobifunctional linker such as disuccinimidyl suberate (DSS) to link an amino function on the peptide or protein to the amino group of a linker on the sequence. By this mechanism, an oligonucleoside-succinimidyl conjugate is formed by reaction of the amino group of the linker on the nucleoside sequence with a disuccinimidyl suberate linker. The disuccinimidyl suberate linker couples with the amine linker on the sequence to extend the size of the linker. The extended linker is then reacted with amine groups such as, for example, the amine of lysine or other available N-terminus amines, on reporter enzymes, peptides and proteins.

Additional objects, advantages, and novel features of this invention will become apparent to those skilled in the art upon examination of the following examples, which are not intended to be limiting.

For the following examples, anhydrous dimethylformamide, cholic acid and N-hydroxysuccinimide were purchased from Aldrich Chemical Co. (Milwaukee, Wis.), ethyl-3-(3-dimethylamino)propylcarbodiimide (EDAC or EDC) was obtained from JBL Scientific (San Luis Obispo, Calif.) as the free base under the label EDAC or from Pierce (Rockford, Ill.) under the label EDC, Aminolink-2 was purchased from ABI and 3'-Amino-Modifier, 5'-Amino-Modifier C6 and Amino-Modifier dT reagents were purchased from Glen Research Corporation. NMR Spectra were run on a Varian Unity-400 instrument. Oligonucleotide synthesis were performed on an Applied Biosystems 380 B or 394 DNA synthesizer following standard phosphoramidite protocols using reagents supplied by the manufacturer. When modified phophoramidites were used, a longer coupling time (10–15 min) was employed. HPLC was performed on a Waters 600E instrument equipped with a model 991 detector. Unless otherwise noted, for analytical chromatography the following conditions were employed: Hamilton PRP-1 column (15×2.5 cm); solvent A: 50 mm TEAA, pH 7.0; solvent B: 45 mm TEAA with 80% $CH_3CN$; flow rate: 1.5 ml/min; gradient: 5% B for the first 5 minutes, linear (1%) increase in B every minute thereafter and for preparative purposes: Waters Delta Pak C-4 column; flow rate: 5 ml/min; gradient: 5% B for the first 10 minutes, linear 1% increase for every minute thereafter.

All oligonucleotide sequences are listed in a standard 5' to 3' order from left to right.

EXAMPLE 1

Cholic Acid N-Hydroxysuccinimide Ester (Compound 1)

Anhydrous DMF (150 ml) was added to a mixture of cholic acid (4.09 g, 15 mmol) and N-hydroxysuccinimide (5.25 g, 45 mmol). The mixture was stirred in the presence of nitrogen. EDAC (4 ml, 25 mmol) was then added and this mixture was then stirred overnight. The solution was then evaporated to a gum and partitioned between 1:1 ethyl acetate and 4% $NaHCO_3$ solution (pH 7.9) (100 ml each). The organic layer was washed with saturated NaCl solution, dried over anhydrous $Na_2SO_4$ and evaporated to yield the title compound as a pale yellow foam (4.6 g, 91%). $^{13}C$ NMR (DMSO-$d_6$) δ12.27, 16.71, 22.58, 22.80, 25.42, 26.19, 27.20, 28.49, 30.41, 30.56, 34.36, 34.82, 34.82, 35.31, 39.09, 39.09, 41.38, 41.53, 45.84, 46.05, 66.25, 70.45, 71.03, 169.28 and 170.16.

EXAMPLE 2

Heterocyclic Base Cholic Acid End-Labeled Oligodeoxynucleotide

An Oligonucleotide of the Sequence:

Oligomer 1: TTG CTT* CCA TCT TCC TCG TC (SEQ ID NO:1)

wherein T* represents a nucleotide functionalized to included a cholic acid linked via a linker to the heterocyclic base of a 2'-deoxyuridine nucleotide was prepared in a 1 μmol scale. Oligomer 1 is useful as an HPV antisense oligonucleotide.

A. Preparation of Intermediate Linker

The linker of the structure —CH=CH—C(O)—NH—$(CH_2)_6$—NH—C(O)—$CF_3$ was introduced via a suitable protected and activated 2'-deoxyuridine phosphoramide intermediate obtained from Glen Research Corporation as Amino-Modifier-dT. The oligonucleotide bearing the linker thereon was deprotected and purified by HPLC.

B. Preparation of Cholic Acid Functionalized Oligonucleotide

An aliquot of the linker bearing oligonucleotide of Example 2-A (approximately 100 O.D. units, 550 nmols) was dissolved in 500 μl of 0.2M $NaHCO_3$ buffer and to this solution cholic acid N-hydroxysuccinimide ester (Compound 1, 75 mg, 149 μmols) was added and heated at 45° C. overnight. It was then passed through a Sephadex G-25 (1.0×25 cm) column. Concentration of the oligonucleotide fractions to 2 ml followed by HPLC purification yielded the desired conjugate wherein cholic acid is internally linked at C-5 of the heterocyclic base.

EXAMPLE 3
5'-Terminus Cholic Acid End-Labeled Oligodeoxynucleotide

A phosphorothioate oligonucleotide having cholic acid attached to its 5'-terminus of the oligonucleotide sequence:

Oligomer 2: 5'-CHA-$C_sT_sG_s$ $T_sC_sT_s$ $C_sC_sA_s$ $T_sC_sT_s$ $T_sC_s$ $A_s$ $C_sT$ (SEQ ID NO:2)

wherein CHA represents cholic acid and the subscript "s" represents a phosphorothioate inter-nucleotide backbone linkage was prepared.

A. Preparation of Intermediate Linker

The oligonucleotide sequence having a 5'-terminus amino group was synthesized on a 3×1.0 μmol scale in the standard manner on the DNA synthesizer utilizing phosphoramidite methodology. The phosphorothioate intra-nucleotide backbone was formed using a phosphorothioate reagent (Beaucage reagent, i.e., 3H-1,2-benzodithioate-3-one 1,1-dioxide; see, Radhakrishnan, et al., *J. Am. Chem. Soc.* 1990, 112, 1253). The Aminolink-2 reagent was used at the last step of the oligonucleotide synthesis. Deprotection with concentrated $NH_4OH$ for 16 hrs at 55° C. yielded the 5'-aminolinker-oligonucleotide.

B. Preparation of Cholic Acid Functionalized Oligonucleotide

The crude 5'-aminolinker-oligonucleotide of Example 3-A (100 O.D. units, approximately 600 nmols based on the calculated extinction coefficient of $1.6756×10^5$ at 260 nm) was dissolved in freshly prepared $NaHCO_3$ buffer (500 μl, 0.2M, pH 8.1) and treated with a solution of cholic acid N-hydroxysuccinimide ester (Compound 1, 75 mg, 149 μmols) dissolved in 200 μl of DMF. The reaction mixture was heated at 45° C. overnight. It was then passed through a Sephadex G-25 (1.0×25 cm) column. Concentration of the oligonucleotide fractions to 2 ml followed by HPLC purification yielded 54 OD units of the desired conjugate (54% yield). HPLC retention times were: 37.42 for the unreacted oligonucleotide and any failure sequences produced during oligonucleotide synthesis and 54.20 for the final product.

EXAMPLE 4
3'-Terminus Cholic Acid End Labeled Oligodeoxynucleotide

A. 3'-Terminus Cholic Acid Oligonucleotide

A phosphorothioate oligonucleotide having cholic acid attached to its 3'-terminus of the oligonucleotide sequence:

Oligomer 3: $C_sT_sG_s$ $T_sC_sT_s$ $C_sC_sA_s$ $T_sC_sC_s$ $T_sC_sT_sT_sC_sA_s$ $C_sT$ 3'-CHA (SEQ ID NO:3)

wherein CHA represents cholic acid and the subscript "s" represents a phosphorothioate inter-nucleotide backbone linkage was prepared.

1. Preparation of Intermediate Linker

The oligonucleotide sequence having a 3'-terminus amino group was synthesized using 3'-amino modifier controlled pore glass (CPG) from Clontech Laboratories (Palo Alto, Calif.) as the solid support. The above-noted Beaucage reagent was utilized to form the phosphorothioate inter-nucleotide backbone. The synthesis was conducted in a "Trityl-Off" mode. The resultant solid support was deprotected with concentrated $NH_4OH$ for 16 hrs at 55° C. Purification on a Sephadex G-25 column yielded a 3'-amino functionalized phosphorothioate oligonucleotide of the specified oligonucleotide sequence.

2. Preparation of Cholic Acid Functionalized Oligonucleotide

The crude oligonucleotide of Example 4-A-1 (50 O.D. units, approximately 300 nmols) was reacted with cholic acid N-hydroxysuccinimide ester (Compound 1, 40 mg) as per the procedure of Example 3. HPLC retention times were 37.45 for the starting oligonucleotide material and 51.68 for the product.

B. 3'-Terminus Cholic Acid Oligonucleotide

A phosphorothioate oligonucleotide having cholic acid attached to its 3'-terminus and of the oligonucleotide sequence:

Oligomer 4: $T_sG_sG_s$ $G_sA_sG_s$ $C_sC_sA_s$ $T_sA_sG_s$ $C_sG_sA_s$ $G_sG_sC$ 3'CHA (SEQ ID NO: 4)

wherein CHA represents cholic acid and the subscript "s" represents a phosphorothioate inter-nucleotide backbone linkage was prepared in the same manner as for the oligonucleotide of Example 4-A-2.

EXAMPLE 5
3'-Terminus Cholic Acid & 5'-Terminus Cholic Acid Di-End-Labeled Oligodeoxynucleotide A phosphorothioate oligonucleotide having cholic acid attached to both of the 3'-terminus and the 5'-terminus of the oligonucleotide sequence:

Oligomer 5: 5'-CHA $C_sT_sG_s$ $T_sC_sT_s$ $C_sC_sA_s$ $T_sC_sT_s$ $T_sC_s$ $A_s$ $C_sT$ 3'-CHA (SEQ ID NO:2)

wherein CHA represents cholic acid and the subscript "s" represents a phosphorothioate inter-nucleotide backbone linkage was synthesized on a 3×1.0 μmol scale. Oligomer 5 has the same sequence as Oligomer 1 except for the cholic acid functionalization.

A. Preparation of Intermediate Linker

The oligonucleotide synthesis was conducted using a 3'-amino modified controlled pore glass (CPG) from Clontech Laboratories as the solid support. Oligonucleotide synthesis was conducted utilizing phosphoramidite synthetic methodology and the Beaucage reagent to form a phosphorothioate inter-nucleotide backbone as per Example 4 above. Upon completion of the basic sequence and while still on the DNA synthesizer, Aminolink-2 reagent was used to introduce a 5'-terminus amino functionality on to the oligonucleotide. Deprotection with concentrated ammonium hydroxide and purification on a Sephadex G-25 column yielded 3',5'-diaminolinker oligonucleotide.

B. Preparation of Cholic Acid Functionalized Oligonucleotide

The crude di-aminolinker oligonucleotide (50 O.D. units, approximately 300 nmols, based on the calculated extinction coefficient of $1.6756×10^5$ at 260 nm) was dissolved in freshly prepared $NaHCO_3$ buffer (500 μl, 0.2M, pH 8.1) and treated with a solution of cholic acid N-hydroxysuccinimide ester (Compound 1, 50 mg, 98.6 μmols) dissolved in 200 μl of DMF. The reaction mixture was heated at 45° C. overnight. It was then passed through a Sephadex G-25 (1.0×25 cm) column. The oligonucleotide fractions were concentrated to 2 ml and purified by reverse phase HPLC. Retention times were 37.76 for unreacted oligonucleotide, 51.65 for 3'-cholic acid conjugated oligonucleotide, 54.34 for 5'-cholic acid conjugated oligonucleotide and 58.75 for 3',5'-di-cholic acid conjugated oligonucleotide. The 58.75 min. product was desalted on a Sephadex G-25 column to yield 11 O.D units (22%) of the desired product.

EXAMPLE 6

3'-Terminus Cholic Acid or 5'-Terminus Cholic Acid Functionalized, 2'-O-Methyl Derivatized Oligodeoxynucleotides Phosphorothioate oligonucleotides having cholic acid attached to either the 3'-terminus end or the 5'-terminus end of the oligonucleotide sequence and further being uniformly functionalized to include a 2'-O-methyl group on each of the nucleotides of the oligonucleotide were synthesized. The following oligonucleotides having uniform 2'-O-methyl substitutions were synthesized:

Oligomer 6: 5'-CHA CCC AGG CUC AGA 3' (SEQ ID NO:5);

Oligomer 7: 5' CCC AGG CUC AGA 3'-CHA (SEQ ID NO:5); and

Oligomer 8: 5'-CHA GAG CUC CCA GGC3' (SEQ ID NO:6).

A. Preparation of Intermediate Linker

Synthesis of the intermediate 5' or 3'-aminolinker oligonucleotide was conducted utilizing 2'-O-methyl phosphoramidite nucleotides available from Chemgenes Inc. (Needham, Mass.) and phosphoramidite chemistry as per Examples 3 and 4 above, respectively. Each of the intermediate oligonucleotides were deprotected in concentrated $NH_4OH$, evaporated and de-salted on a Sephadex G-25 column.

B. Preparation of Cholic Acid Functionalized Oligonucleotide

The resultant crude oligonucleotides from Example 6-A-1 (from 30 to 40 O.D. units, 250–350 nmols based on calculated extinction coefficients of $1.1797 \times 10^5$, $1.1777 \times 10^5$ and $1.1481 \times 10^5$ at 260 nm, respectively for Oligomers 6, 7 and 8) were dried and dissolved in 250 μl of 0.2M $NaHCO_3$ buffer and treated with a solution of cholic acid N-hydroxysuccinimide ester (Compound 1, from 30 to 40 mg, 60 to 80 μmols) dissolved in 500 μl of 0.2 M $NaHCO_3$ buffer and 200 μl DMF and heated between 40–45° C. for 12–24 hrs. The reaction mixtures were evaporated and dissolved in 2 ml of water and washed with 3×2 ml of ethyl acetate. The resultant aqueous solutions were purified by reverse phase HPLC. For Oligomer 6 the HPLC retention times were 34.65 for the starting oligonucleotide material and 58.75 for the product; for Oligomer 7 the HPLC retention times were 37.23 for the starting oligonucleotide material and 55.32 for the product; and for Oligomer 8 the HPLC retention times were 34.99 for the starting oligonucleotide material and 56.98 for the product. The products were evaporated and desalted on a Sephadex G-25 column. The yield averaged about 20% in each case.

EXAMPLE 7

Oligonucleotides Having 2'-Protected-Amine Terminating Linking Group

A. Preparation of 5'-Dimethoxytrityl-2'-(O-Pentyl-N-phthalimido)-2'-Deoxyadenosine Phosphoramidite (Compound 2)

To introduce a functionalization at the 2' position of nucleotides within desired oligonucleotide sequences, 5'-Dimethoxytrityl-2'-(O-pentyl-N-phthalimido)-2'-deoxyadenosine phosphoramidite (Compound 2) was utilized to provide a linking group attached to the 2' position of nucleotide components of an oligonucleotide. Compound 2 was synthesized as per the procedures of patent applications U.S. Ser. Nos. 91/00243 and 463,358, identified above starting from adenosine. Briefly this procedure treats adenosine with NaH in DMF followed by treatment with N-(5-bromopentyl)phthalimide. Further treatment with $(CH_3)_3SiCl$, Ph—CPh—C (O)—Cl and $NH_4OH$ yields N6-benzyl protected 2'-pentyl-N-phthalimido functionalized adenosine. Treatment with DIPA and $CH_2Cl_2$ adds a DMT blocking group at the 5' position. Finally phosphitylation gives the desired phosphoramidite compound, Compound 2. Compound 2 was utilized in the DNA synthesizer as a 0.09M solution in anhydrous $CH_3CN$. Oligonucleotide synthesis was carried out in either an ABI 390B or 394 synthesizer employing the standard synthesis cycles with an extended coupling time of 10 minutes during coupling of Compound 2 into the oligonucleotide sequence. Coupling efficiency of >98% was observed for Compound 2 coupling.

B. 2'-Protected-Amine Linking Group Containing Phosphodiester Oligonucleotides The following oligonucleotides having phosphodiester inter-nucleotide linkages were synthesized:

Oligomer 9: 5' TA*G 3';

Oligomer 10: 5' CCA* G 3';

Oligomer 11: 5' GGC TGA* CTG CG 3' (SEQ ID NO:7);

Oligomer 12: CTG TCT CCA* TCC TCT TCA CT (SEQ ID NO:3); and

Oligomer 13: CTG TCT CCA* TCC TCT TCA* CT (SEQ ID NO:3)

wherein A* represents a nucleotide functionalized to incorporate a pentyl-N-phthalimido functionality. Oligomers 12 and 13 are antisense compounds to the E2 region of the bovine papilloma virus-1 (BPV-1). Oligomers 12 and 13 have the same sequence as Oligomer 3 except for the 2' modification. The oligonucleotides were synthesized in either a 10 μmol scale or a 3×1 μmol scale in the "Trityl-On" mode. Standard deprotection conditions (30% $NH_4OH$, 55° C., 24 hr) were employed. The oligonucleotides were purified by reverse phase HPLC (Waters Delta-Pak $C_4$ 15 μm, 300A, 25×100 mm column equipped with a guard column of the same material). They were detritylated and further purified by size exclusion using a Sephadex G-25 column. NMR analyses by both proton and phosphorus NMR confirmed the expected structure for the Oligomers 9 and 10.

C. 2'-Protected-Amine Linking Group Containing Phosphorothioate Oligonucleotides The following oligonucleotides having phosphorothioate inter-nucleotide linkages were synthesized:

Oligomer 14: $T_sT_sG_s\ C_sT_sT_s\ C_sC_sA^*_s\ T_sC_sT_s\ T_sC_sC_s\ T_sC_sG_s\ T_sTC$ (SEQ ID NO:1);

Oligomer 15: $T_sG_sG_s\ G_sA_sG_s\ C_sC_sA_s\ T_sA_sG_s\ C_sG_sA^*_s\ G_sG_sC$ (SEQ ID NO:4); and Oligomer 16: $T_sG_sG_s\ G_sA^*_sG_s\ C_sC_sA^*_s\ T_sA^*_sG_s\ C_sG_sA^*_s\ G_sG_sC$ (SEQ ID NO:4)

wherein A* represents a nucleotide functionalized to incorporate a pentyl-N-phthalimido functionality and the subscript "s" represents a phosphorothioate inter-nucleotide backbone linkage. Oligomer 14 is an antisense compound directed to the E2 region of the bovine papilloma virus-1 (BPV-1). Oligomers 15 and 16 are antisense compounds to ICAM. Oligomer 14 has the same sequence as Oligomer 3 except for the 2' modification whereas Oligomers 15 and 16 have the same sequence as Oligomer 4 except for the 2' modification. These oligonucleotides were synthesized as per the method of Example 7-B except during the synthesis, for oxidation of the phosphite moieties, the Beaucage reagent (see Example 3 above) was used as a 0.24 M solution in anhydrous $CH_3CN$ solvent. The oligonucleotides were synthesized in the "Trityl-On" mode and purified by reverse phase HPLC utilizing the purification procedure of Example 7-B.

D. 2'-O-Methyl Derivatized, 2'-Protected-Amine Linking Group Containing RNA Oligonucleotides The following oligonucleotides having 2'-O-methyl groups on each nucleotide not functionalized with a 2'-protected amine functionalization were synthesized:

Oligomer 17: CCA A*GC CUC AGA (SEQ ID NO:8); and

Oligomer 18: CCA GGC UCA GA*T (SEQ ID NO:9)

wherein A* represents a nucleotide functionalized to incorporate a pentyl-N-phthalimido functionality and where the remaining nucleotides except the 3'-terminus nucleotide are each 2'-O-methyl derivatized nucleotides. The 3'-terminus nucleotide in both Oligomers 17 and 18 is a 2'-deoxy nucleotide. Both Oligomers 17 and 18 are antisense compounds to the HIV-1 TAR region. The oligonucleotides were synthesized as per the method of Example 6 utilizing Compound 2 for introduction of the nucleotides containing the pentyl-N-phthalimido functionality and appropriate 2-O-methyl phosphoramidite nucleotides from Chemgenes Inc. (Needham, Mass.) for the remaining RNA nucleotides. The 3'-terminus terminal 2'-deoxy nucleotides were standard phosphoamidites utilized for the DNA synthesizer. The oligonucleotides were deprotected and purified as per the method of Example 7-B.

EXAMPLE 8

Functionalization Of Oligonucleotides At the 2' Position

A. Functionalization with Biotin

1. Single Site Modification

About 10 O.D. units ($A_{260}$) of Oligomer 12 (see Example 7) (approximately 60 nmols based on the calculated extinction coefficient of $1.6756 \times 10^5$) was dried in a microfuge tube. The oligonucleotide was dissolved in 200 µl of 0.2 M $NaHCO_3$ buffer and D-biotin-N-hydroxysuccinimide ester (2.5 mg, 7.3 µmols) (Sigma, St. Louis, Mo.) was added followed by 40 µl DMF. The solution was let stand overnight. The solution was applied to a Sephadex G-25 column (0.7×15 cm) and the oligonucleotide fractions were combined. Analytical HPLC showed nearly 85% conversion to the product. The product was purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 mins., linear (1%) increase in B every minute thereafter) and further desalted on Sephadex G-25 to give the oligonucleotide:

Oligomer 19: CTG TCT CCA* TCC TCT TCA CT (SEQ ID NO:3)

wherein A* represents a nucleotide functionalized to incorporate a biotin functionality linked via a 2'-O-pentyl-amino linking group to the 2' position of the designated nucleotide. HPLC retention times are shown in Table 1 below.

2. Multiple Site Modification

About 10 O.D. units ($A_{260}$) of Oligomer 13 (see Example 7, approximately 60 nmols) was treated utilizing the method of Example 8-A-1 with D-biotin-N-hydroxysuccinimide ester (5 mg) in 300 µl of 0.2 M $NaHCO_3$ buffer/50 µl DMF. Analytical HPLC showed 65% of double labeled oligonucleotide product and 30% of single labeled products (from the two available reactive sites). HPLC and Sephadex G-25 purification gave the oligonucleotide:

Oligomer 20: CTG TCT CCA* TCC TCT TCA* CT (SEQ ID NO:3)

wherein A* represents nucleotides functionalized to incorporate a biotin functionality linked via a 2'-O-pentyl-amino linking group to the 2' position of the designated nucleotide. HPLC retention times for this product (and its accompanying singly labeled products) are shown in Table 1 below.

B. Functionalization with Fluorescein

1. Single Site Modification

A 1M $Na_2CO_3$/1M $NaHCO_3$ buffer (pH 9.0) was prepared by adding 1M $NaHCO_3$ to 1 M $Na_2CO_3$. 200 µl of this buffer was added to 10 O.D. units of Oligomer 12 (see Example 7) in a microfuge tube. 10 mg of fluorescein-isocyanate in 500 µl DMF was added to give a 0.05 M solution. 100 µl of the fluorescein solution was added to the oligonucleotide solution in the microfuge tube. The tube was covered with aluminum foil and let stand overnight. The reaction mixture was applied to a Sephadex G-25 column (0.7×20 cm) that had been equilibrated with 25% (v/v) ethyl alcohol in water. The column was eluted with the same solvent. Product migration could be seen as a yellow band well separated from dark yellow band of the excess fluorescein reagent. The fractions showing absorption at 260 nm and 485 nm were combined and purified by HPLC as per the purification procedure of Example 8-A-1. Analytical HPLC indicated 81% of the desired doubly functionalized oligonucleotide. The product was lyophilized and desalted on Sephadex to give the oligonucleotide:

Oligomer 21: CTG TCT CCA* TCC TCT TCA CT (SEQ ID NO:3)

wherein A* represents a nucleotide functionalized to incorporate a fluorescein functionality linked via a 2'-O-pentyl-amino linking group to the 2' position of the designated nucleotide. HPLC retention times are shown in Table 1 below.

2. Multiple Site Modification

10 O.D. units ($A_{260}$) of Oligomer 13 (from Example 7) was dissolved in 300 µl of the 1M $Na_2HCO_3$/1M $Na_2CO_2$ buffer of Example 8-B-1 and 200 µl of the fluorescein-isothiocyanate stock solution of Example 8-B-1 was added. The resulting solution was treated as per Example 8-B-1. Analytical HPLC indicated 61% of doubly labeled product and 38% of singly labeled products. Work up of the reaction gave the oligonucleotide:

Oligomer 22: CTG TCT CCA* TCC TCT TCA* CT (SEQ ID NO:3)

wherein A* represents nucleotides functionalized to incorporate a fluorescein functionality linked via a 2'-O-pentyl-amino linking group to the 2' position of the designated nucleotide. HPLC retention times are shown in Table 1 below.

C. Functionalization with Cholic Acid

1. Single Site Modification

10 O.D. units ($A_{260}$) of Oligomer 12 (see Example 7) was treated with cholic acid-NHS ester (Compound 1, 5 mg, 9.9 µmols) in 200 µl of 0.2 M $NaHCO_3$ buffer/40 µl DMF. The reaction mixture was heated for 16 hrs at 45° C. The product was isolated as per the method of Example 8-A-1. Analytical HPLC-indicated >85% product formation. Work up of the reaction gave the oligonucleotide:

Oligomer 23: CTG TCT CCA* TCC TCT TCA CT (SEQ ID NO:3)

wherein A* represents a nucleotide functionalized to incorporate a cholic acid functionality linked via a 2'-O-pentyl-amino linking group to the 2' position of the designated nucleotide. HPLC retention times are shown in Table 1 below.

2. Multiple Site Modification

10 O.D. units ($A_{260}$) of Oligomer 13 (see Example 7) was treated with cholic acid-NHS ester (Compound 1, 10 mg, 19.8 µmols) in 300 µl of 0.2 M $NaHCO_3$ buffer/50 µl DMF.

The reaction mixture was heated for 16 hrs at 45° C. The product was isolated as per the method of Example 8-A-1. Analytical HPLC revealed 58% doubly labeled product, 17% of a first singly labeled product and 24% of a second singly labeled product. Work up as per Example 8-A-1 gave the oligonucleotide:

Oligomer 24: CTG TCT CCA* TCC TCT TCA* CT (SEQ ID NO:3)

wherein A* represents nucleotides functionalized to incorporate a cholic acid functionality linked via a 2'-O-pentyl-amino linking group to the 2' position of the designated nucleotide. HPLC retention times are shown in Table 1 below.

D. Functionalization with Digoxigenin

1. Single Site Modification

10 O.D. units ($A_{260}$) of Oligomer 12 (see Example 7) was treated with digoxigenin-3-O-methylcarbonyl-ε-aminocaproic N-hydroxy succinimide ester (Boehringer Mannheim Corporation, Indianapolis, Ind.) in 200 μl of 0.1 M borate pH 8.3 buffer/40 μl DMF. The reaction mixture was let stand overnight. The product was isolated as per the method of Example 8-A-1. Work up of the reaction gave the oligonucleotide:

Oligomer 25: CTG TCT CCA* TCC TCT. TCA CT (SEQ ID NO:3)

wherein A* represents a nucleotide functionalized to incorporate a digoxigenin functionality linked via a 2'-O-pentyl-amino linking group to the 2' position of the designated nucleotide. HPLC retention times are shown in Table 1 below.

2. Multiple Site Modification

10 O.D. units ($A_{260}$) of Oligomer 13 (see Example 7) was treated with digoxigenin-3-O-methylcarbonyl-ε-aminocaproic N-hydroxy succinimide ester (Boehringer Mannheim Corporation, Indianapolis, Ind.) in 300 μl of 0.1 M borate pH 8.3 buffer/50 μl DMF. The reaction mixture was let stand overnight. The product was isolated as per the method of Example 8-A-1. Work up as per Example 8-A-1 gave the oligonucleotide:

Oligomer 26: CTG TCT CCA* TCC TCT TCA* CT (SEQ ID NO:3)

wherein A* represents nucleotides functionalized to incorporate a cholic acid functionality linked via a 2'-O-pentyl-amino linking group to the 2' position of the designated nucleotide. HPLC retention times are shown in Table 1 below.

TABLE 1

HPLC Retention Times Of Oligonucleotides Functionalized At 2' Position

| Oligomer | Retention Time Minutes | | |
|---|---|---|---|
| | Mono Substitution | Multiple | Substitution |
| Oligomer 12[1] | 21.78 | | |
| Oligomer 13[1] | | 22.50 | |
| Oligomer 19[2] | 23.58 | | |
| Oligomer 20[2] | | 24.16[a] | 25.19[b] |
| Oligomer 21[3] | 26.65 | | |
| Oligomer 22[3] | | 26.99[a] | 29.33[b] |
| | | 27.55[a] | |
| Oligomer 23[4] | 30.10 | | |
| Oligomer 24[4] | | 30.38[a] | 37.00[b] |
| | | 32.22[a] | |
| Oligomer 25[5] | 28.06 | | |
| Oligomer 26[5] | | 28.14[a] | 33.32[b] |
| | | 29.24[a] | |

Conditions: Waters 600E with 991 detector, Hamilton PRP-1 column 0.7 × 15 cm; solvent A: 50 mM TEAA pH 7.0; B: 45 mM TEAA with 80% acetonitrile: 1.5 ml flow rate: Gradient: 5% B for first 5 mins., linear (1%) increase in B every minute thereafter;
[a]Mono conjugated minor product;
[b]Doubly conjugated major product;
[1]Parent Oligonucleotide - no 2' functionalization;
[2]2' Biotin functionalization;
[3]2' Fluorescein functionalization;
[4]2' Cholic Acid functionalization; and
[5]2' Digoxigenin functionalization.

EXAMPLE 9

Functionalization Of Oligonucleotide at the 2' Position with Reporter Enzymes, Peptides and Proteins A. Use of Heterobifunctional Linker 1. Synthesis of Oligonucleotide-Maleimide Conjugate Oligomer 12 (Example 7)(100 O.D. units, 600 nmols) is lyophilized in a 5 ml pear-shaped flask. Sulfo-SMCC reagent, Pierce Chemical Co. (Rockford, Ill.) (16 mg, 46 μmols) is dissolved in phosphate buffer (800 μl, 0.1M, pH 7.0) and added to the oligonucleotide bearing flask. An additional 200 μl of buffer are used to wash the reagent and transfer it to the oligonucleotide flask. The contents of the flask are stirred overnight and loaded on to a Sephadex G-25 column (1×40 cm) equipped with a fraction collector. The oligonucleotide-maleimide conjugate containing fractions are collected and tested by analytical HPLC for separation from other NHS type products.

2. Synthesis of Oligonucleotide-Peptide Conjugate

An aliquot of the oligonucleotide-maleimide conjugate of Example 9-A-1 (about 50 O.D. units, 300 nmols) is lyophilized in a microfuge tube. SV40 peptide (pro-asp-lys-lys-arg-lys-cys)(2.5 mg, about 2.5 μmols) is taken up in phosphate buffer (800 μl, 0.1 M, pH 7.0) and added to the oligonucleotide-maleimide conjugate containing tube. The contents of the tube are stirred overnight under an argon atmosphere. The reaction mixture is passed through a Sephadex G-25 column and the oligonucleotide-peptide conjugate fractions are identified by HPLC. Isolation of the product from product-bearing fractions via HPLC and desalting on Sephadex G-25 will yield an oligonucleotide of the sequence:

Oligomer 27: CTG TCT CCA TCC TCT TCA CT (SEQ ID NO:3)

wherein A* represents a nucleotide functionalized to incorporate a SV40 peptide functionality linked via a 2'-O-pentyl-amino-sulfo-SMCC (sulfosuccinimidyl-4-(N-maleimidomethyl)cyclohexane-1-carboxylate) linking group to the 2' position of the designated nucleotide.

B. Use of Homobifunctional Linker

1. Synthesis of Oligonucleotide-Disuccinimidyl Suberate Conjugate

An aliquot (10 O.D. units, 60 nmols) of Oligomer 12 (Example 7) is evaporated to dryness and is dissolved in freshly prepared 0.1 M $NaHCO_3$/50 mM EDTA (100 μl, pH 8.25). The solution is then treated with a solution of DSS, Pierce Chemical Co. (Rockford, Ill.) (2.6 mg, 7 μmol) in 200 μl DMSO. The solution is stored at room temperature for 15 minutes and then immediately applied to a Sephadex G-25 column (1×40 cm) that is previously packed and washed with water at 4° C. The oligonucleotide fractions are combined immediately in a 25 ml pear-shaped flask and are rapidly frozen in dry ice/isopropyl alcohol and lyophilized to a powder.

2. Synthesis of Oligonucleotide-Protein Conjugate

A solution of calf intestinal alkaline phosphatase (Boehringer Mannheim) (20.6 mg, 2.06 ml, 147 nmol) is spun at 4° C. in a Centricon microconcentrator at 6000 rpm until the volume is less than 50 μl. It is then redissolved in 1 ml of cold Tris buffer (pH 8.5, 0.1M containing 0.1 NaCl and 0.05 M $MgCl_2$) and concentrated twice more. Finally the concentrate is dissolved in 400 μl of the same buffer. This solution is added to the activated oligonucleotide from Example 9-B-1 and the solution stored for 18 hrs at room temp. The product is diluted to approximately 30 ml and applied to a Sephadex G-25 column (1×20 cm, chloride form) maintained at 4° C. The column is eluted with 50 nM Tris-Cl pH 8.5 until the UV absorbance of the fractions eluted reach near zero values. The column is then eluted with a NaCl salt gradient 0.05 M to 0.75 M (150 ml each). The different peaks are assayed for both oligonucleotide and alkaline phosphatase activity and the product bearing fractions are combined. Typically the first peak will be excess enzyme, the second peak the oligonucleotide-protein conjugate and the third peak unreacted oligonucleotide. Isolation of the product from the product-bearing fractions via HPLC and desalting on Sephadex G-25 will yield an oligonucleotide of the sequence:

Oligomer 28: CTG TCT CCA* TCC TCT TCA CT (SEQ ID NO:3)

wherein A* represents a nucleotide functionalized to incorporate an alkaline phosphatase functionality linked via an 2'-O-pentyl-amino-sulfo-SMCC (sulfosuccinimidyl-4-(N-maleimidomethyl)cyclohexane-1-carboxylate) linking group to the 2' position of the designated nucleotide.

EXAMPLE 10
Heterocyclic Base Peptide-Conjugated Oligonucleotides

Utilizing the method of Example 9-A-1 the intermediate amino linker oligonucleotide of Example 2-A is reacted with sulfo-SMCC reagent. The isolated oligonucleotide-maleimide conjugate is then further reacted with SV40 peptide as per Example 9-A-2. This will give an oligonucleotide of the structure:

Oligomer 29: TTG CTT* CCA TCT TCC TCG TC (SEQ ID NO:1)

wherein T* represents a nucleotide functionalized to include a peptide linked via an extended linker to the heterocyclic base of a 2'-deoxyuridine nucleotide.

EXAMPLE 11
3'-Terminus Protein-Conjugated Oligonucleotides

Utilizing the method of Example 9-B-1 the 2'-O-methyl derivatized intermediate amino linker oligonucleotide of Example 6-A is reacted with DSS reagent. The isolated oligonucleotide-disuccinimidyl suberate conjugate is then further reacted with a lysine containing Nuclease RNase H using the method of Example 9-B-2. This will give an oligonucleotide of the structure:

Oligomer 30: $C_sC_sC_s\ A_sG_sG_s\ C_sU_sC_s\ A_sG_s$A-3'-protein (SEQ ID NO:5)

wherein protein represents RNase H, the subscript "s" represents a phosphorothioate inter-nucleotide backbone linkage and each of the nucleotides of the oligonucleotide includes a 2'-O-methyl group thereon.

EXAMPLE 12

5'-Terminus Protein-Conjugated 2'-O-Methyl Derivatized Oligonucleotides

Utilizing the method of Example 9-B-1 the 2'-O-methyl derivatized intermediate amino linker oligonucleotide of Example 6-A (Oligomer 6) is reacted with DSS reagent. The isolated oligonucleotide-disuccinimidyl suberate conjugate is then further reacted with a lysine containing Staphylococcal Nuclease using the method of Example 9-B-2. This will give an oligonucleotide of the structure:

Oligomer 31: 5'-protein-$C_sC_sC_s\ A_sG_sG_s\ C_sU_sC_s\ A_sG_s$A 3' (SEQ ID NO:5)

wherein protein represents Staphylococcal Nuclease, the subscript "s" represents a phosphorothioate inter-nucleotide backbone linkage and each of the nucleotides of the oligonucleotide includes a 2'-O-methyl group thereon.

PROCEDURE A
Confirmation of Structure of Functionalized Oligonucleotides Containing A Tethered 2'-Amino Moiety Oligonucleotides of the invention were digested with snake venom phosphodiesterase and calf-intestine alkaline phosphatase to their individual nucleosides. After digestion, the nucleoside composition was analyzed by HPLC. The HPLC analysis established that functionalized nucleotide compounds having the tethered 2'-amino moiety thereon were correctly incorporated into the oligonucleotide.

Snake venom phosphodiesterase [Boehringer-Mannheim cat. #108260, 1 mg (1.5 units)/0.5 ml] and alkaline phosphatase from calf intestine (1 unit/microliter, Boehringer-Mannheim cat. #713023) in Tris-HCl buffer (pH 7.2, 50 mM) were used to digest the oligonucleotides to their component nucleosides. To 0.5 O.D. units of oligonucleotide in 50 μl buffer (nearly 40 μM final concentration for a 20 mer) was added 5 μl of snake venom phosphodiesterase (nearly 0.3 units/mL, final concentration) and 10 μl of alkaline phosphatase (app. 150 units/mL, final concentration). The reaction mixture was incubated at 37° C. for 3 hours. Following incubation, the reaction mixture was analyzed by HPLC using a reverse phase analytical column (app. 30×2.5 cm); solvent A: 50 mM TEAA pH 7; solvent B: acetonitrile; gradient 100% for 10 mins, then 5% B for 15 mins, then 10% B and then wash. The results of these digestion are shown in Table 2 for representative oligonucleotides.

TABLE 2

OLIGONUCLEOTIDE ANALYSIS VIA ENZYMATIC DIGESTION

| | | Observed Ratios** | | | |
|---|---|---|---|---|---|
| Oligomer | Abs. max. C | 267 G | 252 T | 267 A* | 260 A |
| Oligomer 10 | 2 | 1 | | 1 | |
| Oligomer 11 | 3 | 5 | 2 | 1 | |
| Oligomer 12 | 9 | 1 | 8 | 1 | 1 |
| Oligomer 13 | 9 | 1 | 8 | 2 | |

*Nucleoside having 2'-O-linker attached thereto; and
**Corrected to whole numbers.

As is evident from Table 2, the correct nucleoside ratios are observed for the component nucleotides of the test oligonucleotides.

PROCEDURE B
Determination of Melting Temperatures (Tm's) of Cholic Acid Oligonucleotide Conjugates The relative ability of oligonucleotides to bind to their complementary strand is compared by determining the melting temperature of the hybridization complex of the oligonucleotide and its complementary strand. The melting temperature (Tm), a characteristic physical property of double helices, denotes the temperature in degrees centigrade at which 50% helical versus coil (un-hybridized) forms are present. Tm is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the Tm, the greater the strength of the binding of the strands. Non-Watson-Crick base pairing has a strong destabilizing effect on the Tm. Consequently, absolute fidelity of base pairing is necessary to have optimal binding of an antisense oligonucleotide to its targeted RNA.

1. Terminal End Conjugates a. Synthesis

A series of oligonucleotides were synthesized utilizing standard synthetic procedures (for un-functionalized oligonucleotides) or the procedure of Example 3-A above for oligonucleotides having a 5'-terminus amino linker bearing oligonucleotide or the procedure of Example 3-B for 5'-terminus cholic acid-bearing oligonucleotides. Each of the oligonucleotides had the following 5-LO antisense sequence: 5' TCC AGG TGT CCG CAT C3'. The nucleotides were synthesized on a 1.0 μmol scale. Oligomer 32 was the parent compound having normal phosphodiester internucleotide linkages. Oligomer 33 incorporated phosphorothioate inter-nucleotide linkages in the basic oligonucleotide sequence. Oligomer 34 is a an intermediate oligonucleotide having a 5'-aminolink at the 5'-terminus of the basic oligonucleotide sequence and Oligomer 35 was a similar 5'-aminolink compound incorporating phosphorothioate inter-nucleotide linkages. Oligomer 36 is a 5'-terminus cholic acid conjugate of the basic phosphodiester oligonucleotide sequence while Oligomer 37 is a similar 5'-cholic acid conjugate incorporating phosphorothioate inter-nucleotide linkages. Oligomers 32 and 33 were synthesized in a "Trityl-On" mode and were purified by HPLC. Oligomers 34 and 35 were synthesized as per Example 30-A above without or with Beaucage reagent treatment, to yield phosphodiester or phosphorothioate inter-nucleotide linkages, respectively. Oligomers 36 and 37 were prepared from samples of Oligomers 34 and 35, respectively, utilizing a solution of cholic acid N-hydroxysuccinimide ester (Compound 1) 1 dissolved in DMF as per Example 3-B. Oligomers 36 and 37 were purified by HPLC. The products were concentrated and desalted in a Sephadex G-25 column. Gel electrophoresis analyses also confirmed a pure product with the pure conjugate moving slower than the parent oligonucleotide or 5'-amino functionalized oligonucleotide.

b. Melting Analysis

The test oligonucleotides [either the phosphodiester, phosphorothioate, cholic acid conjugated phosphodiester, cholic acid conjugated phosphorothioate or 5'-aminolink intermediate phosphodiester or phosphorothioate oligonucleotides of the invention or otherwise] and either the complementary DNA or RNA oligonucleotides were incubated at a standard concentration of 4 uM for each oligonucleotide in buffer (100 mM NaCl, 10 mM Na-phosphate, pH 7.0, 0.1 mM EDTA). Samples were heated to 90 degrees C and the initial absorbance taken using a Guilford Response II spectrophotometer (Corning). Samples were then slowly cooled to 15 degrees C and then the change in absorbance at 260 nm was monitored during the heat denaturation procedure. The temperature was elevated 1 degree/absorbance reading and the denaturation profile analyzed by taking the 1st derivative of the melting curve. Data was also analyzed using a two-state linear regression analysis to determine the Tm's. The results of these tests are shown in Table 3 as are the HPLC retention times of certain of the test compounds.

TABLE 3

Melting Temperature Of The Hybridization Complex Of The Oligonucleotide And Its Complementary Strand

| Oligomer | Tm** | | HPLC Ret. Time* |
|---|---|---|---|
| | DNA | RNA | minutes |
| 32 | 62.6 | 62.0 | — |
| 33 | 55.4 | 54.9 | — |
| 34 | ND | ND | 13.6 |
| 35 | ND | ND | 17.0 |
| 36 | 63.4 | 62.4 | 22.0 |
| 37 | 56.3 | 55.8 | 22.5 |

*HPLC conditions: Walters Delta Pak C-18 RP 2.5 u column; at 0 min 100% 0.1 TEAA; at 30 min 50% TEAA and 50% Acetonitrile: Flow rate 1.0 ml/min.
**Tm at 4 μM each strand from fit of duplicate melting curves to 2-state model with linear sloping base line. Conditions: 100 mM NaCl, 10 mM Phosphate, 0.1 mM EDTA, pH 7.0.
ND = not determined As is evident from Table 2, conjugates of cholic acid at the end of the oligonucleotide do not affect the Tm of the oligonucleotides.

2. Strands Incorporating 2'-O-Pentylamino Linker a. Synthesis

An oligonucleotide of the sequence:

Oligomer 38: GGA* CCG GA*A* GGT A*CG A*G (SEQ ID NO:11)

wherein A* represents a nucleotide functionalized to incorporate a pentylamino functionality at its 2'-position was synthesized in a one micromole scale utilizing the method of Example 7-B. The oligonucleotide was purified by reverse phase-HPLC, detrytylated and desalted on Sephadex G-25. PAGE gel analysis showed a single band. A further oligonucleotide, Oligomer 39, having the same sequence but without any 2'-O-amino linker was synthesis in a standard manner. A complementary DNA oligonucleotide of the sequence:

Oligomer 40: CCT GGC CTT CCA TGC TC (SEQ ID NO:12) was also synthesized in a standard manner as was a complementary RNA oligonucleotide of the sequence:

Oligomer 41: CCU GGC CUU CCA UGC UC (SEQ ID NO:13)

b. Melting Analysis

Melting analysis was conducted as per the method of Procedure B-1-b. The results are shown in Table 4.

TABLE 4

Melting Temperature Of The Hybridization Complex Of The Oligonucleotide And Its Complementary Strand

| Oligomer | Tm* | |
|---|---|---|
| | DNA[1] | RNA[2] |
| 38 | 54.5 | 58.0 |
| 39 | 60.6 | 56.9 |

*Tm at 4 μM each strand from fit of duplicate melting curves to 2-state model with linear sloping base line. Conditions: 100 mM NaCl, 10 mM Phosphate, 0.1 mM EDTA, pH 7.0.
[1]Against DNA complementary strand, Oligomer 40.
[2]Against RNA complementary strand, Oligomer 41

As is evident from Table 4 against the RNA complementary strand the change in Tm's between the strand having 2'-amino linkers thereon and the unmodified strand is 1.1 degrees (0.22 change per modification). Against the DNA strand, the change is −6.1 degrees (−1.2 change per modification). When compared to the parent unmodified oligonucleotide the 2'-amino linker-containing strand has a stabilizing effect upon hybridization with RNA and a destabilizing effect upon hybridization with DNA.

Compounds of the invention were tested for their ability to increase cellular uptake. This was determined by judging either their ability to inhibit the expression of bovine papilloma virus-1 (BPV-1) or an assay involving luciferase production (for HIV-1).

PROCEDURE C

Determination of Cellular Uptake Judged by the Inhibition of Expression of Bovine Papilloma Virus-1 (bpv-1) as Measured by an E2 Transactivation Assay For this test, a phosphorothioate oligonucleotide analog of the sequence:

Oligomer 42: CTG TCT CCA TCC TCT TCA CT (SEQ ID NO:3)

was used as the basic sequence. This sequence is designed to be complementary to the translation initiation region of the E2 gene of bovine papilloma virus type 1 (BPV-1). Oligomer 42 served as the positive control and standard for the assay. Oligomer 3 (from Example 4 above) served as a second test compound. It has the same basic sequence except it is a phosphorothioate oligonucleotide and further it has a cholic acid moiety conjugated at the 3'-end of the oligonucleotide. Oligomer 2 (from Example 2 above) served as a third test compound. Again it is of the same sequence, it is a phosphorothioate oligonucleotide and it has a cholic acid moiety conjugated at the 5'-end. Oligomer 5 (from Example 5 above) served as a fourth test compound. Once again it has the same sequence, is a phosphorothioate oligonucleotide and it has a cholic acid moiety conjugated at both the 3'-end and 5'-end. A fifth test compound was a phosphorothioate oligonucleotide with no significant sequence homology with BPV-1. A sixth test compound was a further phosphorothioate oligonucleotide with no significant sequence homology with BPV-1. The last test compound, the seventh test compound, was a phosphorothioate oligonucleotide with cholic acid conjugated to the 3'-end but having no significant sequence homology with BPV-1. Compounds five, six and seven served as negative controls for the assay.

For each test I-38 cells were plated at 5×10⁴ cells per cm² in 60 mm petri dishes. Eight hours after plating, medium was aspirated and replaced with medium containing the test oligonucleotide and incubated overnight. Following incubation, medium was aspirated and replaced with fresh medium without oligonucleotide and incubated for one hour. Cells were then transfected by the CaPO₄ method with 2 ug of pE2RE-1-CAT. After a four hour incubation period cells were glycerol shocked (15% glycerol) for 1 minute followed by washing 2 times with PBS. Medium was replaced with DMEM containing oligonucleotide at the original concentration. Cells were incubated for 48 hours and harvested. Cell lysates were analyzed for chloramphenicol acetyl transferase by standard procedures. Acetylated and nonacetylated $^{14}$C-chloramphenicol were separated by thin layer chromatography and quantitated by liquid scintillation. The results are expressed as percent acetylation.

Two lots of the positive control compound were found to acetylate at a level of 29% and 30%. The negative controls, test compounds five, six and seven, were found to acetylate at 59%, 58% and 47%, respectively. The 3'-cholic acid conjugate test compound, Oligomer 3, was found to acetylate to 23%, the 5'-cholic acid conjugate test compound, Oligomer 2, was found to acetylate to 36% and the test compound conjugated at both the 3'-end and the 5'-end, Oligomer 5, was found to acetylate to 27%.

The results of this test suggests that placement of a cholic acid moiety at the 3'-terminus of an oligonucleotide increase the activity. This in turn suggests that the increased activity was the result of increased cellular membrane transport.

PROCEDURE D

Determination of Cellular Uptake Judged by Inhibition of pHIVluc With Cholic Acid Linked 2'-O-Methyl Substituted Oligonucleotides For this test the absence of an oligonucleotide in a test well served as the control. All oligonucleotides were tested as 2'-O-methyl analogs. For this test an oligonucleotide of the sequence:

Oligomer 43: CCC AGG CUC AGA (SEQ ID NO:5)

where each of the nucleotides of the oligonucleotide includes a 2'-O-methyl substituent group served as the basic test compound. The second test compound of the sequence:

Oligomer 44: 5'-CHA CCC AGG CUC AGA (SEQ ID NO:5)

wherein CHA represents cholic acid and where each of the nucleotides of the oligonucleotide includes a 2'-O-methyl substituent group, was also of the same sequence as the first test compound. This second test compound included cholic acid conjugated to its 5'-end and was prepared as per the method of Example 3 utilizing 2'-O-methyl phosphoramidite intermediates as identified in Example 7-C. The third test compound of the sequence:

Oligomer 45: CCC AGG CUC AGA 3'-CHA (SEQ ID NO:5)

wherein CHA represents cholic acid and where each of the nucleotides of the oligonucleotide includes a 2'-O-methyl substituent group was also of the same sequence as the first test compound. The third test compound included cholic acid conjugated to its 3'-end and was prepared as per the method of Example 4 utilizing 2'-O-methyl phosphoramidite intermediates as identified in Example 7-C. The fourth test compound was a 2'-O—Me oligonucleotide of a second sequence:

Oligomer 46: GAG CUC CCA GGC (SEQ ID NO:6)

where each of the nucleotides of the oligonucleotide includes a 2'-O-methyl substituent group. The fifth test compound was of sequence:

Oligomer 47: 5'-CHA GAG CUC CCA GGC (SEQ ID NO:6)

wherein CHA represents cholic acid and where each of the nucleotides of the oligonucleotide includes a 2'-O-methyl substituent group. It was of the same sequence as the fifth test compound. This test compound included cholic acid conjugated to its 5'-end and was prepared as per the method of Example 3 utilizing 2'-O-methyl phosphoramidite intermediates as identified in Example 7-C. A sixth test compound was a randomized oligonucleotide of the sequence:

Oligomer 48: CAU GCU GCA GCC (SEQ ID NO:14)

HeLa cells were seeded at $4 \times 10^5$ cells per well in 6-well culture dishes. Test oligonucleotides were added to triplicate wells at 1 $\mu$M and allowed to incubate at 37° C. for 20 hours. Medium and oligonucleotide were then removed, cells washed with PBS and the cells were $CaPO_4$ transfected. Briefly, 5 $\mu$g of pHIVluc, a plasmid expressing the luciferase cDNA under the transcriptional control of the HIV LTR constructed by ligating the KpnI/HindIII restriction fragments of the plasmids pT3/T71uc and pHIVpap (NAR 19(12)) containing the luciferase cDNA and the HIV LTR respectively, and 6 $\mu$g of pcDEBtat, a plasmid expressing the HIV tat protein under the control of the SV40 promoter, were added to 500 $\mu$l of 250 mM $CaCl_2$, then 500 $\mu$l of 2xHBS was added followed by vortexing. After 30 minutes, the $CaPO_4$ precipitate was divided evenly between the six wells of the plate, which was then incubated for 4 hours. The media and precipitate were then removed, the cells washed with PBS, and fresh oligonucleotide and media were added. Incubation was continued overnight. Luciferase activity was determined for each well the following morning. Media was removed, then the cells washed 2x with PBS. The cells were then lysed on the plate with 200 $\mu$l of LB (1% Trit X-100, 25 mM Glycylglycine pH 7.8, 15 mM $MgSO_4$, 4 mM EGTA, 1mM DTT). A 75 $\mu$l aliquot from each well was then added to a well of a 96 well plate along with 75 $\mu$l of assay buffer (25 mM Glycylglycine pH 7.8, 15 mM $MgSO_4$, 4 mM EGTA, 15 mM $KPO_4$, 1 mM DTT, 2.5 mM ATP). The plate was then read in a Dynatec multiwell luminometer that injected 75 $\mu$l of Luciferin buffer (25 mM Glycylglycine pH 7.8, 15 mM $MgSO_4$, 4 mM EGTA, 4 mM DTT, 1 mM luciferin) into each well, immediately reading the light emitted (light units).

The random sequence compound (Oligomer 48) and the other non-cholic acid-conjugated test compounds (Oligomers 43 and 46) had comparable activity. The 5'-conjugate of the first sequence (Oligomer 44) also had activity comparable to the non-conjugated compounds. The 5'-conjugate of the second sequence (Oligomer 47) showed a three-fold increase in activity compared to the non-conjugated compounds and the 3'-conjugate of the first sequence (Oligomer 45) showed a further 3-fold increase in activity compared to Oligomer 47.

All the test cholic acid-bearing oligonucleotides showed significant inhibition of luciferase production compared to non-cholic acid-bearing oligonucleotides. This suggests that the increased activity was the result of increased cellular membrane transport of the cholic acid-bearing test oligonucleotides.

EXAMPLE 13

Retinoic Acid Conjugated Oligonucleotide

A. Retinoic Acid N-Hydroxysuccinimide Ester

Anhydrous DMF (150 ml) was added to a mixture of retinoic acid (15 mmol, 4.5 g, Fluka) and N-hydroxysuccinimide (5.25 g, 45 mmol). The mixture was stirred in the presence of argon. EDAC [ethyl-3-(3-dimethylamino)propyl carbodiimide] (4 ml, 25 nmol) was then added and this mixture was then stirred overnight. The solution was then evaporated to a yellow gum and dissolved in 200 ml ethylacetate and washed successively with 4% $NaHCO_3$ solution (200 ml) followed by saturated NaCl solution, dried over anhydrous $MgSO_4$ and evaporated to yield the desired compound as a yellow solid in nearly 90% yield.

B. Retinol Phosphoramidite

All-trans-retinol (1 g) was vacuum dried and dissolved in anhydrous $CH_2Cl_2$ (10 ml) in an argon atmosphere. Diisopropylethylamine (2.65 ml, 21.5 mmol) was syringed in and the reaction mixture was cooled in an ice-bath. 2-cyanoethyl-N, N-diisopropylchlorophosphoramidate (2.5 g, 2.45 ml, 10.5 mmol) was slowly added by syringe under argon atmosphere. The reaction mixture was stirred for 30 min. at which time TLC ($CH_2Cl_2$:$CH_3OH$:$Et_3N$, 90:10:0.1) indicated complete conversion of the alcohol to its phosphoramidite. The reaction mixture was added to 100 ml of saturated $NaHCO_3$ followed by washing the reaction flask with (2x25 ml) $CH_2Cl_2$. The $CH_2Cl_2$ layer was separated and washed with 100 ml of saturated NaCl solution and dried over anhydrous $MgSO_4$ and evaporated into a yellow foam. The amidite was used directly in the DNA synthesizer without further purification since decomposition of this amidite was noted upon silica column purification.

C. Retinoic Acid Functionalized Oligonucleotide

Multiple batches of an oligonucleotide of the sequence:

Oligomer 49: $T_sG_sG_s$ $G_sA_sG_s$ $C_sC_sG_s$ $T_sA_sG_s$ $C_sG_sA_s$ $G_sG_sC_s$-3'AL (SEQ ID NO:15)

wherein AL represents a 3'-aminolinker and "s" represents a phosphorothioate inter-nucleotide backbone linkage were synthesized as per the procedure of Example 4 on 10 $\mu$mol scales in the standard manner on the DNA synthesizer utilizing phosphoramidite methodology employing 3'-amine-ON solid support available from Clontech. During the synthesis, the phosphorothioate backbone was formed by the Beaucage reagent. The oligonucleotide was deprotected and purified using standard protocols.

The 3'-aminolinker-oligonucleotide (Oligomer 49, 100 OD units, approximately 550 nmols) was dissolved in freshly prepared NaHCO3 buffer (500 $\mu$l, 0.2M, pH 8.1) and treated with a solution of retinoic acid N-hydroxy succinimide ester (50 mg, 125 $\mu$mols) dissolved in 500 $\mu$l of DMF. The reaction mixture was covered with aluminum foil and left at 37° C. bath overnight. It was then passed through a Sephadex G-25 column (1x40 cm) and the first eluant was collected, concentrated and passed again through another Sephadex G-25 column (1x40 cm) to remove excess Vitamin-A reagent. Concentration of the yellow oligonucleotide fractions followed by HPLC purification yielded the retinoic acid-oligonucleotide conjugate.

EXAMPLE 14

Folic Acid Conjugated Oligonucleotide

A mixture of folic acid (30 mg, 68 $\mu$mols) and 1-hydroxybenzotriazole (30 mg, 222 $\mu$mols) was dissolved in 900 ml of dry DMF. To this solution, 50 ml of EDAC (312 $\mu$mols) was added. The resultant yellow viscous material was vortexed well and 500 ml from the solution was transferred into 100 O.D. units of the 3'-aminolinker oligonucleotide (Oligomer 49, 537 $\mu$mols) dissolved in 0.2M $NaHCO_3$ buffer. The yellow solution was vortexed, covered with aluminum foil and allowed to react for 16 hrs. The mixture was then loaded into a Sephadex G-25 column (1x40 cm). The oligonucleotide fraction was collected, concentrated and passed one more time through Sephadex G-25 column. The oligonucleotide fractions were concentrated and purified by reverse phase HPLC. The conjugate appeared as a broad peak centered around 32.5 min. while the oligonucleotide starting material had a retention time of 30 min. (5%–40% of 100% CH$_3$CN over 60 min. as solvent B and 50 mM TEAA pH 7.0 as the solvent A in reverse phase HPLC). The conjugate was concentrated and passed through Sephadex G-25 column again for desalting. Gel analysis indicated a slower moving material than the starting oligonucleotide.

EXAMPLE 15
Methyl Folate Conjugated Oligonucleotide

In a like manner to Example 14, 5-methyl folate was also attached to Oligomer 49.

EXAMPLE 16
Pyridoxal Conjugated Oligonucleotide

The 3'-aminolinker-oligonucleotide (Oligomer 49, 20 O.D. units, approximately 110 nmols, based on the calculated extinction coefficient of 1.828×10$^5$ at 260 nm) was dissolved in 100 microliters of water. 100 ml of 1M NaOAc buffer (pH 5.0) was added followed by 5 mg of pyridoxal hydrochloride (24 μmols) and 50 μl of 60 mM NaCNBH$_3$ solution. The solution was vortexed and left aside for overnight. It was then passed through a Sephadex G-25 column and further purified in an analytical HPLC column.

EXAMPLE 17
Tocopherol Conjugated Oligonucleotide

A. Vitamin E (Tocopherol)-Hemisuccinate-NHS Ester

α-Tocopherolhemisuccinate (Sigma, 5 g, 9.4 mmols) was treated with 3 equivalents of N-hydroxysuccinimide and 2 equivalents of EDAC as described under the vitamin-A NHS ester synthesis, Example 13-A above. Work up in the same manner as Example 13 yielded the title compound as a light brown wax-like solid.

B. Tocopherol Conjugated Oligonucleotide

α-Tocopherol-hemisuccinate-NHS ester was treated with Oligomer 49 in the same manner described in Example 13-C for the retinoic acid conjugation. The conjugate was obtained in nearly 50% yield.

EXAMPLE 18
Synthesis of Uridine Based Aminolinkers

A. Preparation of 5'-dimethoxytrityl-2'-(O-pentyl-N-phthalimido)uridine Phosphoramidite Utilizing the protocol of Wagner, et al., *J. Org. Chem.* 1974, 39, 24, uridine (45 g, 0.184 mol) was refluxed with di-n-butyltinoxide (45 g, 0.181 mol) in 1.4 l of anhydrous methanol for 4 hrs. The solvent was filtered and the resultant 2',3'-O-dibutylstannylene-uridine was dried under vacuum at 100° C. for 4 hrs to yield 81 g (93%).

The 2',3'-O-dibutyl stannylene-uridine was dried over P$_2$O$_5$ under vacuum for 12 hrs. To a solution of this compound (20 g, 42.1 mmols) in 500 ml of anhydrous DMF were added 25 g (84.2 nmols) of N(5-bromopentyl) phthalimide (Trans World Chemicals, Rockville, Md.) and 12.75 g (85 mmols) of cesium fluoride (CeF) and the mixture was stirred at room temperature for 72 hrs. The reaction mixture evaporated, coevaporated once with toluene and the white residue was partitioned between EtOAc and water (400 ml each). The EtOAC layer was concentrated and applied to a silica column (700 g). Elution with CH$_2$Cl$_2$—CH$_3$O—H (20:1 v/v) gave fractions containing a mixture of the 2'- and 3'-isomers of O-pentyl-ω-N-phthalimido uridine, in 50% yield.

The mixture was allowed to react with DMT chloride in dry pyridine at room temperature for 6 hrs. CH$_3$OH was used to quench excess DMT-Cl and the residue was partitioned between CH$_2$Cl$_2$ containing 0.5% Et$_3$N and water. The organic layer was dried (MgSO$_4$) and the residue was applied to a silica column. Elution with CH$_2$Cl$_2$:CH$_3$OH (20:1, v/v) separated the 2' and 3' isomers.

The 2'-O-pentyl-ω-N-phthalimido-5'-DMT-uridine was converted to its phosphoramidite as per the procedure referenced in Example 7.

B. Preparation of 5'-dimethoxytrityl-2-(O-hexyl-N-phthalimido)uridine Phosphoramidite In a like manner to Example 18-A, using N-(6-bromohexyl) phthalimide, a 2'-six carbon aminolinker was introduced at the 2'-position of uridine.

C. Preparation of 5'-dimethoxytrityl-2-(O-decyl-N-phthalimido)uridine Phosphoramidite In a like manner to Example 18-A N-(10-bromodecyl) phthalimide was similarly used to introduce a 2'-ten carbon aminolinker in the nucleotide.

EXAMPLE 19
Synthesis of Cytidine Based Aminolinkers

A. Preparation of 5'-dimethoxytrityl-2-(O-propyl-N-phthalimido)cytidine Phosphoramidite The 5'-DMT protected 2'-O-functionalized cytidine phosphoramidite was prepared as per the procedure of Example 7 substituting cytidine for adenosine.

B. Preparation of Oligonucleotides Having a 2'-Aminolinker Bearing 3'-Terminal Nucleotide The following oligonucleotides having phosphodiester inter-nucleotide linkages and a 2'-aminolinker at the 3' terminal nucleotide were synthesized:

Oligomer 50: GGC GUC UCC AGG GGA UCU GAC* (SEQ ID NO:16)

Oligomer 51: TCT GAG TAG CAG AGG AGC TC (SEQ ID NO:17)

wherein C* represents a nucleotide functionalized to incorporate a propyl-N-phthalimido functionality. Oligomer 50 is antisense to the Cap region of CMV and Oligomer 51 is antisense to an ICAM sequence. The oligonucleotides were synthesized on a 3 μmol scale. Upon completion of synthesis they were deprotected using standard protocols and purified by reverse phase HPLC, detritylated and desalted.

EXAMPLE 20
Conversion of an Oligonucleotide Having a 2'-Aminolinker to an Oligonucleotide Having a Thiolinker A. Oligomer 50

Oligomer 50 (25 O.D. units) was treated with 5 mg SATA (N-succinimidyl-S-acetylthioacetate) in 0.2M NaHCO$_3$ buffer. The reaction mixture was passed through a Sephadex G-25 column, the oligonucleotide fraction was concentrated and treated with 200 mM NH$_2$OH hydrochloride solution in water (1 ml).

B. Oligomer 51

Oligomer 51 (25 O.D. units) was treated with 5 mg SATA (N-succinimidyl-S-acetylthioacetate) in 0.2M NaHCO$_3$ buffer. The reaction mixture was passed through a Sephadex G-25 column, the oligonucleotide fraction was concentrated and treated with 200 mM hydroxylamine hydrochloride solution in water (1 ml).

EXAMPLE 21
Conjugation of o-Phenanthroline at 2'-Position of Oligonucleotides A. Oligomer 52

To the solution resulting from Example 20-A was added 2 mg of 5-(iodoacetamide)-o-phenanthroline reagent followed by shaking overnight. The conjugate was purified by a size exclusion column and reverse phase HPLC to yield Oligomer 52: GGC GUC UCC AGG GGA UCU GAC-2'PHA (SEQ ID NO:16) wherein PHA represents a nucleotide functionalized at its 2'-position with phenanthroline via a thiol linker of the structure 2'-O—(CH$_2$)$_3$—NH—C(=O)—CH$_2$—S—CH$_2$—C(=O)—NH—.

B. Oligomer 53

To the solution resulting from Example 20-A was added 2 mg of 5-(iodoacetamide)-O-phenanthroline reagent followed by shaking overnight. The conjugate was purified by a size exclusion column and reverse phase HPLC to yield Oligomer 53: TCT GAG TAG CAG AGG AGC TC-2'PHA (SEQ ID NO:17) wherein PHA represents a nucleotide functionalized at its 2'-position with phenanthroline via a thiol linker of the structure 2'-O—(CH$_2$)$_3$—NH—C(=O)—CH$_2$—S—CH$_2$—C(=O)—NH—

EXAMPLE 22

Oligonucleotide Having a Nucleotide with a Crosslinker/Alkylator Attached Via a 2'-Aminolinker in a Internal Position in the Oligonucleotide A. Synthesis of an oligonucleotide having a uridine 2'-aminolinker The following oligonucleotide having phosphodiester inter-nucleotide linkages and a 2'-aminolinker at an internal position is synthesized utilizing the uridine 2'-aminolinker of Example 18:

Oligomer 54: GGC CAG AUC UGA GCC UGG GAG CU*C UGU GGC C (SEQ ID NO:18) wherein U* represents a nucleotide functionalized to incorporate a propyl-N-phthalimido functionality. Oligomer 50 is an oligonucleotide corresponding to positions $G_{16}$ to $C_{46}$ of TAR RNA.

B. Conjugation of iodo acetamide to $U_{38}$ position of TAR structure

Oligomer 54 is reacted with iodoacetic acid N-hydroxysuccinimide ester to form the iodoacetamide derivative at the $U_{38}$ position of the TAR structure. The $U_{38}$ position is thus available for crosslinking to the 7 position of the guanine base of either $G_{26}$ or $G_{28}$ of the TAR structure.

EXAMPLE 23

Conjugation of Pyrene at 2'-Position of Oligonucleotides

A. Single 2' Site Modification

10 O.D. units ($A_{260}$) of Oligomer 12 (Example 7-B) (approximately 60 nmols based on the calculated extinction coefficient of $1.68\times10^5$) was dried in a microfuge tube. It was dissolved in 200 $\mu$ml of 0.2 M NaHCO$_3$ buffer and pyrene-1-butyric acid N-hydroxysuccinimide ester (i.e., succinimidyl-1-pyrene butyrate, 3 mg, 7.79 $\mu$mols, Molecular Probes, Eugene, Oregon) was added followed by 400 $\mu$l of DMF. The mixture was incubated at 37° C. overnight. The solution was applied to a Sephadex G-25 column (1×40 cm) and the oligonucleotide fractions were combined. The product was purified by HPLC. The pyrene conjugates exhibited the typical pyrene absorption between 300 and 400 nm. The product had a HPLC retention time of 26.94 min. while the parent oligonucleotide had a retention time of 21.78 min. (Waters 600E with 991 detector; Hamilton PRP-1 column (15×25 cm); Solvent A: 50 mM TEAA, pH 7.0; B: 45 mM TEAA with 80% Acetonitrile; 1.5 mL/min. flow rate: Gradient 5% B for first 5 minutes, linear (1%) increase in B every minute afterwards).

B. Multiple 2' Site Modifications

10 O.D. units of Oligomer 12 (Example 7-B) was treated with twice the amount of pyrene-1-butyric acid N-hydroxysuccinimide (6 mg in 400 $\mu$l DMF) and worked up in the same fashion as Example 23-A. Sephadex G-25 purification followed by HPLC purification gave the doubly pyrene-conjugated oligonucleotide. The doubly conjugated oligonucleotide exhibited a HPLC retention time of 32.32 min. while the parent oligonucleotide had a retention time of 21.78 min. (Waters 600E with 991 detector; Hamilton PRP-1 column (15×25 cm); Solvent A: 50 mM TEAA, pH 7.0; B: 45 mM TEAA with 80% Acetonitrile; 1.5 mL/min. flow rate: Gradient 5% B for first 5 minutes, linear (1%) increase in B every minute afterwards).

EXAMPLE 24

Conjugation of Acridine at 2'-Position of Oligonucleotides

A. Single 2' Site Modification

10 O.D. units ($A_{260}$) of Oligomer 12 (Example 7-B, about 60 nmols) was dried and dissolved in 1M NaHCO$_3$/Na2CO$_3$ buffer, pH 9.0, 200 $\mu$l. 9-acridinyl-isothiocyante, (5 mg, 2.1 $\mu$mols, Molecular Probes, Eugene, Oreg.) was dissolved in 200 $\mu$l DMF. This solution was added to the oligonucleotide, vortexed, covered with aluminum foil and left at 37° C. overnight. The reaction mixture was purified by passing through a Sephadex G-25 column (1×40 cm) concentrated and further purified by HPLC (reverse-phase). The product had a HPLC retention time of 25.32 min. while the parent oligonucleotide had a retention time of 21.78 min. (Waters 600E with 991 detector; Hamilton PRP-1 column (15×25 cm); Solvent A: 50 mM TEAA, pH 7.0; B: 45 mM TEAA with 80% Acetonitrile; 1.5 mL/min. flow rate: Gradient 5% B for first 5 minutes, linear (1%) increase in B every minute afterwards).

B. Multiple 2' Site Modifications

10 O.D. units ($A_{260}$) of Oligomer 13 (Example 7-B) in 400 $\mu$l of 1M Na2CO$_3$/NaHCO$_3$ buffer (pH 9.0) was treated with 10 mg of 9-acridinyl-isothiocyanate in 400 $\mu$l of DMF. The reaction mixture was vortexed, covered with aluminum foil and left at 37° C. overnight. The reaction mixture was purified as for the single site reaction of Example 24-A. The doubly conjugated acridine-oligonucleotide eluted as the last peak in the HPLC following single-modification products. The product had a HPLC retention time of 32.32 min. while the parent oligonucleotide had a retention time of 21.78 min. (Waters 600E with 991 detector; Hamilton PRP-1 column (15×25 cm); Solvent A: 50 mM TEAA, pH 7.0; B: 45 mM TEAA with 80% Acetonitrile; 1.5 mL/min. flow rate: Gradient 5% B for first 5 minutes, linear (1%) increase in B every minute afterwards).

EXAMPLE 25

Conjugation of Porphyrin at 2'-Position of Oligonucleotides

Methylpyroporphyrin XX1 ethyl ester (Aldrich) is condensed with aminocaproic acid using N-hydroxysuccinimide and EDAC. The resultant carboxylic acid is then activated again with N-hydroxy succinimide and EDAC and treated with Oligomer 12 as per the procedure of Example 23-A to give the 2'-porphyrin conjugated oligonucleotide.

EXAMPLE 26

Conjugation of Hybrid Intercalator-Ligand at 2'-Position of Oligonucleotides

A. Photonuclease/intercalator ligand

The photonuclease/intercalator ligand 6-[[[9-[[6-(4-nitrobenzamido)hexyl]amino]acridin-4-yl]carbonyl]amino] hexanoyl-pentafluorophenyl ester was synthesized as per the procedure of Egholm et al., *J. Am. Chem. Soc.* 1992, 114, 1895.

B. Single 2' site modification

10 O.D. units of Oligomer 12 (Example 7-B) was dissolved in 100 μl of 0.1 M borate buffer (pH 8.4) and treated with 330 μl of DMF solution (10 mg in 1 ml of DMF) of 6-[[[9-[[6-(4-nitrobenzamido)hexyl]amino]acridin-4-yl]carbonyl]amino]hexanoylpentafluorophenyl ester. The solution was covered with aluminum foil and allowed to react overnight. The product was purified by Sephadex G-25 and HPLC purification of the reaction mixture.

C. Multiple 2' site modification

10 O.D. units $A_{260}$ of Oligomer 13 (Example 7-B) was dissolved in 200 μl of 0.1 M borate buffer (pH 8.4) and treated with 660 μl of the DMF solution of 6-[[[9-[[6-(4-nitrobenzamido)hexyl]amino]acridin-4-yl]carbonyl]amino]hexanoylpentafluorophenyl ester (10 mg in 1 ml solution) and the solution was covered with aluminum foil and left aside overnight. The bright yellow solution was purified by Sephadex G-25 and reverse phase HPLC to give the doubly conjugated oligonucleotide.

EXAMPLE 27

Conjugation of Bipyridine Complex at 2'-Position of Oligonucleotides

A. Bipyridine Complex

Succinimidyl-4-carboxyl-4'-methyl-2,2'-bipyridine is synthesized according to the procedure of Telser, et al., J. Am. Chem. Soc. 1989, 111, 7221.

B. Single 2' Site Modification

10 O.D. $A_{260}$ units of Oligomer 12 is reacted with a 200 fold molar excess of succinimidyl-4-carboxyl-4'-methyl-2,2'-bipyridine in 0.1 M borate buffer pH 8.5/DMF. The solution is purified by Sephadex G-25 and reverse phase HPLC to yield the conjugated oligonucleotide.

EXAMPLE 28

Conjugation of Aryl Azide Photocrosslinkers at 2'-Position of Oligonucleotides

A. Conjugation of N-hydroxysuccinimidyl-4-azidobenzoate (HSAB)

Oligomer 14 (i.e., TTG CTT CCA* TCT TCC TCG TC (SEQ ID NO:1) wherein A* represents 2'-O-pentyl amino adenosine, Example 7-C, 100 O.D. units, 595 nmols, based on the calculated extinction coefficient of $1.6792 \times 10^6$ OD units) was dried and dissolved in 500 ml of 0.2M NaHCO$_3$ buffer pH 8.1 and treated with 25 mg of N-hydroxysuccinimidyl-4-azidobenzoate (HSAB, 96 μmols, available both from Pierce & Sigma)) dissolved in 500 μl of DMF. The reaction was allowed to react overnight at 37° C. and passed twice over Sephadex G-25 column (1×40 cm). The oligonucleotide fraction was purified by reverse-phase HPLC. The product had the HPLC retention time of 38.79 min while the parent oligonucleotide had the retention time of 33.69 min. (5%→40% CH3CN in 60 min.) in reverse phase column.

B. Conjugation of N-succinimidyl-6(4'-azido-2'-nitrophenyl-amino)hexanoate

Oligomer 14 (Example 7-C, 200 OD units) was dissolved in 500 ml NaHCO$_3$ buffer (0.2M, pH 8.1) and treated with 500 mg of N-succinimidyl-6(4'-azido-2'-nitrophenyl-amino)hexanoate (SANPAH, 128 μmols, available both from Pierce and Sigma) dissolved in 500 μl DMF. The reaction vial was wrapped with aluminum foil and heated at 37° C. overnight. The reaction mixture was passed twice over a Sephadex G-25 column (1×40 cm). The oligonucleotide fraction was purified by reverse-phase HPLC. The product had the HPLC retention time of 40.69 min. while the parent oligonucleotide had the retention time of 33.69 min. (5%→40% CH$_3$CN in 60 min.) in a reverse phase column.

PROCEDURE D

Duplex Melting Temperature of Conjugated Oligonucleotides

Utilizing the protocol described in Procedure B-1-b, the melting temperatures of various of the 2-aminolinked conjugate oligomers of the invention against a complementary DNA strand were obtained. The conjugate oligomers were compared to an oligomer of the same sequence bearing a 2'-O-pentylamino group. An un-modified, i.e., wild type, strand of the same sequence was also tested for comparison purposes. Both single site and multiple site conjugated oligomers were tested. As is shown in Table 5, the $T_m$ and the $\Delta T_m$/modification, both as compared to 2'-pentylamino bearing oligomer, were measured. The wild type sequence is:

Oligomer 55: CTG TCT CCA TCC TCT TCA CT (SEQ ID NO:2)

the single site sequence is:

Oligomer 12: CTG TCT CCA* TCC TCT TCA CT (SEQ ID NO:3)

and the multiple site sequence is:

Oligomer 13: CTG TCT CCA* TCC TCT TCA* CT (SEQ ID NO:3) where A* represents a site of conjugation.

TABLE 5

| Duplex Melting Temperature of Conjugated Oligonucleotides Against DNA | | | |
|---|---|---|---|
| Oligomer | Conjugate | $T_m$ ° C. | $\Delta T_m$/mod |
| 55 | wild type | 60.5 | — |
| 12 | 2'-O-pentyl-NH$_2$ | 58.1 | — |
| 12 | biotin | 56.4 | −1.7 |
| 12 | cholic acid | 55.5 | −2.6 |
| 12 | digoxigenin | 55.8 | −2.3 |
| 12 | fluorescein | 55.1 | −3.0 |
| 12 | pyrene | 62.6 | +4.5 |
| 12 | acridine | 58.6 | +0.5 |
| 13 | 2'-O-pentyl-NH$_2$ | 56.9 | — |
| 13 | biotin | 54.4 | −1.3 |
| 13 | cholic acid | 54.3 | −1.3 |
| 13 | digoxigenin | 53.8 | −1.6 |
| 13 | fluorescein | 53.4 | −1.8 |
| 13 | pyrene | 65.1 | +4.1 |
| 13 | acridine | 58.1 | +1.2 |

EXAMPLE 29

Conjugation of Imidazole-4-Acetic Acid at 2'-Position of Oligonucleotides

A. Activated imidazole-4-acetic acid

Imidazole-4-acetic acid was reacted with 2,4-dinitrofluoro benzene. The resulting imidazole-N-(DNP)-4-acetic acid was converted to its N-hydroxy succinimide ester by treating with NHS/EDAC as per the procedure of Example 13.

B. 2'-Site Modification

10 O.D. $A_{260}$ units of oligomer 12 was reacted with a 100 fold molar excess of imidazole-N-(DNP)-4-acetic acid NHS ester in O.1M borate buffer pH 8.5/DMF (200 μL each). After overnight reaction, the reaction mixture was treated with 200 μL of mercaptoethanol to cleave off the DNP protecting group. The resulting reaction mixture was purified by passing through a Sephadex G-25 column followed by reverse phase HPLC to yield the imidazole conjugated oligonucleotide.

EXAMPLE 30
Conjugation of Metal Chelating Agents to 2'-Position of Oligonucleotide A. EDTA Complex To form an EDTA Fe(II) complex for coupling to an oligonucleotide as a nucleic acid cleaving agent, tricylohexyl ester of EDTA is synthesized according to the procedure of Sluka, et al., *J. Am. Chem. Soc.* 1990, 112, 6369.

B. EDTA 2'-Site Modification

The tricyclohexyl ester of EDTA (1.25 mg, 1.94 mmol) and hydroxybenzotriazole (HOBt, 1 mg, 6.6 mmol) are dissolved in DMF (50 µL) and $EDAC_{10}$ µL is added. To this solution, oligonucleotide 12 (10 OD units) in 100 µL g 0.1M borate buffer is added and left overnight. The solution is passed through a Sephadex G-25 column and the oligonucleotide fraction treated with conc. $NH_3$ (100 µL) for 1 hr. to cleave off the acid protecting groups. Finally purification is effected by size exclusion and HPLC.

C. DTPA 2'-Site Modification

Oligomer 12 was treated with diethylene triamine pentaacetic anhydride (DTPA) in 0.1M $NaHCO_3$/DMF to offer single-site modification. The conjugate was complexed with Gadolinium ion (Gd III) to give a contrast agent, usable among other uses, as an uptake measuring agent.

EXAMPLE 31
Conjugation of Cholesterol To The 2'-Position of Oligonucleotide

A. Method 1–2'-Aminolinker

Cholesterol-hemisuccinate was converted to its N-hydroxy succinimide ester. It was then conjugated to Oligomer 12 as per the procedure of Example 23-A or Oligomer 13 as per the procedure of Example 23-B.

B. Method 2—Conjugation of Cholesterol via a Disulfide Bridge

Step 1

Thiocholesterol (1.4 g, 3.5 mmol) is added to a stirred solution of 2,2'-dithiobis(5-nitropyridine) (1.4 g 4 mmol) in chloroform 20 mL containing glacial acetic acid (400 µL) under an argon atmosphere. The reaction is allowed to continue overnight at room temperature, after which the precipitated 5-nitropyridine-2-thione was removed and the solution evaporated and purified in a silica column to give S-(2-thio-5-nitropyridyl)-thio cholesterol.

Step 2

Oligomer 55: $T_sG_sG_s\ G_sA_sG_s\ C_sC_sG_s\ T_sA^*_sG_s\ C_sG_sA_s\ G_sG_sC_s$ (SEQ ID NO:15)
wherein A* represents an adenosine nucleotide funtionalized to incorporate a 2'-O-pentylamino linking group is synthesized as per Example 7. This oligonucleotide is then converted into a thiol linker compound as per the procedure described for Oligomer 50 in Example 20.

The thiol linker group containing oligonucleotide, Oligomer 55, is reacted with an excess of S-(2-thio-5-nitropyridyl)-thiocholesterol to conjugate the cholesterol moiety to the 2' position of the oligonucleotide via a disulfide bridge.

EXAMPLE 32
Synthesis of 2'-Aminolinker Containing Solid Supports for DNA/RNA Synthesis A. 5'-Dimethyoxytrityl-2'-O-(pentyl-N-phthalimido) uridine 5'-Dimethyoxytrityl-2'-O-(pentyl-N-phthalimido)uridine was synthesized as per the procedure described in Example 18.

B. Succinate Nucleoside

The nucleoside of step A (1 mmol) was treated with 4-DMAP (122 mg, 1 mmol) and succinic anhydride (250 mg, 2.5 mmol) in 10 mL g anhydrous pyridine. After shaking overnight, TLC (EtOAc: Hexane 6:4 with 0.1% $Et_3N$) indicated complete succinylation of the nucleoside. 10 mL of water was added and the reaction shaken for an additional 1 hr. The reaction mixture was evaporated and partitioned between $CHCl_3$ and 20% citric acid (50 mL each). The chloroform layer was washed with brine and evaporated. It was then used in the next step.

C. Nitrophenyl Succinate

The dry 3'-O-succinate from step B was dissolved in dry dioxan (10 mL) containing pyridine (400 ml). 4-Nitrophenol (280 mg, 2 mmol) was added followed by DCC (1.32 g, 5 mmol) and the solution was shaken for 24 hrs. The fine precipitate of urea was filtered and the filtrate evaporated and applied to a silica column. The column was eluted with 5% $CH_3OH$ in $CHCl_3$ containing 0.1% $Et_3N$. The 3'-nitrophenyl succinate of the nucleoside eluted first from the column. The product containing fractions were evaporated to give a foam.

D. Nucleoside Solid Support

The 3'-nitrophenyl succinate from step C was dissolved in 5 mL of anhydrous DMF and treated with 5 g of 500*A pore diameter aminopropyl CPG support and shaken for 8 hrs. The CPG support was filtered, washed with methanol (5×20 ml) followed by ether (5×20) and dried. The CPG support was capped by treating for 30 min. with pyridine/acetic anhydride/N-methyl imidazole (20 ml, 8:1:1 v/v/v). The CPG support was then filtered off, washed with pyridine, methanol and ether and air-dried. Assay of the dimethoxy trityl showed the loading capacity of the CPG support was 27 mmols/gram.

PROCEDURE E
Determination of Cellular Uptake of Folic Acid Conjugated Oligonucleotide The effect of conjugation of an oligonucleotide with folic acid was determined by the inhibition of ICAM-1 utilizing the method of Chiang, et al., *J. Biol. Chem.* 1991, 266, 18162. Utilizing this method, human lung epithelial carcinoma cells (A549 cells) were grown to confluence in 96 well plates. Medium was removed and the cells were washed with folic acid free medium three times. Folic acid free medium was added to the cells and increasing concentrations of an ICAM-1 specific antisense phosphorothioate oligonucleotide having the sequence 5'-TGG GAG CCA TAG CGA GGC-3' (SEQ ID NO:4), either free or conjugated to folic acid, was added to the incubation medium. This oligonucleotide is an 18 base phosphorothioate oligonucleotide that targets the AUG translation initiation codon of the human ICAM-1 mRNA (Chiang et al., *J. Biol. Chem.* 1991, 266, 18162). The oligonucleotides were incubated with the A549 cells for 24 hours then ICAM-1 was induced by adding 2.5 ng/ml tumor necrosis factor-α to the medium. Cells were incubated an additional 15 hours in the presence of tumor necrosis factor-α and oligonucleotide. ICAM-1 expression was determined by a specific ELISA as described by Chiang, et al. We had previously demonstrated that the addition of the test oligonucleotide to incubation medium alone does not result in inhibition of ICAM-1 expression. However formulation of the test oligonucleotide with cationic liposomes results in at least a 1000 fold increase in potency and also correlates with the appearance of the oligonucleotide in the nucleus (Bennett, et al., *Molecular Pharmacology* 1991, 41, 1023). The results of this test are shown in Table 6. At the 30 uM level, the folic acid conjugated oligonucleotide shows an approximate 40% enhancement in activity.

TABLE 6

| Concentration | ICAM-1 Activity | |
|---|---|---|
| | Oligonucleotide Control | Oligonucleotide + Folic Acid – Percent Of Control |
| 1 uM | 105.1 | 107.6 |
| 3 uM | 112.0 | 104.4 |
| 10 uM | 112.4 | 92.9 |
| 30 uM | 108.4 | 61.6 |

TABLE 6-continued

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound comprising a plurality of linked nucleosides, wherein at least one of said nucleosides is functionalized at its 2'-position by attachment of a steroid molecule, a reporter molecule, a water soluble vitamin, an RNA cleaving complex, a porphyrin, an alkylator, a hybrid photonuclease, or an aryl azide photo-crosslinking agent.

2. A method of effecting cellular uptake of a compound having a plurality of linked nucleosides, comprising contacting an organism with said compound wherein said compound includes at least one heterocyclic base functionalized nucleoside having a steroid molecule, an enzyme, a peptide, a protein, or a vitamin, linked to the heterocyclic base of the nucleoside.

3. The method of claim 2 wherein said heterocyclic base functionalized nucleoside is functionalized with a steroid molecule.

4. The method of claim 2 wherein said heterocyclic base functionalized nucleoside is functionalized with an enzyme, a peptide or a protein.

5. The method of claim 2 wherein said heterocyclic base functionalized nucleoside is functionalized with a vitamin.

6. A method of effecting cellular uptake of a compound having a plurality of linked nucleosides, comprising contacting an organism with said compound wherein said compound includes at least one inter-strand nucleoside having a steroid molecule, an enzyme, a peptide, a protein, or a vitamin linked to an inter-strand linkage linking said inter-strand nucleoside to an adjacent nucleoside.

7. The method of claim 6 wherein said inter-strand nucleoside has a steroid molecule linked to an inter-strand linkage linking said inter-strand nucleoside to an adjacent nucleoside.

8. The method claim 7 wherein said inter-strand linkage is not the inter-strand linkage between the first and the second nucleosides at the 3' terminus or the 5' terminus of said oligonucleotide.

9. The method of claim 6 wherein said inter-strand nucleoside has an enzyme, a peptide or a protein linked to an inter-strand linkage linking said inter-strand nucleoside to an adjacent nucleoside.

10. The method claim 6 wherein said inter-strand nucleoside has a vitamin linked to an inter-strand linkage linking said inter-strand nucleoside to an adjacent nucleoside.

* * * * *